Figure 1:
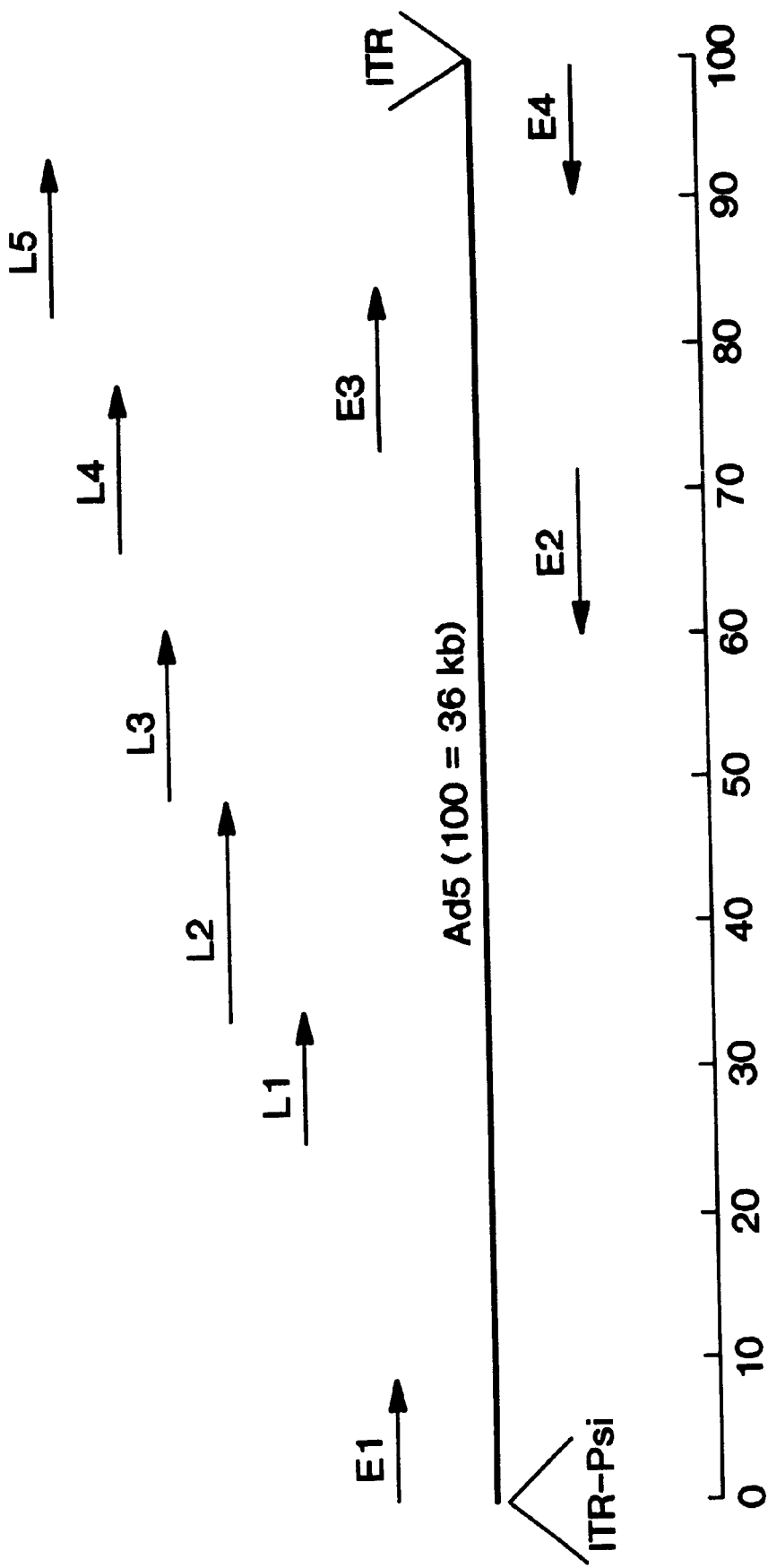

United States Patent [19]
Vigne et al.

[11] Patent Number: 6,127,175
[45] Date of Patent: Oct. 3, 2000

[54] CELLS FOR THE PRODUCTION OF RECOMBINANT ADENOVIRUSES

[75] Inventors: Emmanuelle Vigne, Ivry sur Seine; Michel Perricaudet, Ecrosnes; Jean-François Dedieu, Paris; Cécile Orsini, Paris; Patrice Yeh, Paris; Martine Latta, Charenton le Pont; Edouard Prost, Sucy en Brie, all of France

[73] Assignee: Rhone-Poulenc Rorer S.A., Antony Cedex, France

[21] Appl. No.: 08/875,223

[22] PCT Filed: Jan. 19, 1996

[86] PCT No.: PCT/FR96/00088

§ 371 Date: Jul. 17, 1997

§ 102(e) Date: Jul. 17, 1997

[87] PCT Pub. No.: WO96/22378

PCT Pub. Date: Jul. 25, 1996

[30] Foreign Application Priority Data

Jan. 20, 1995 [FR] France ................................. 95 00747
Jun. 1, 1995 [FR] France ................................. 95 06532
Sep. 8, 1995 [FR] France ................................. 95 10541

[51] Int. Cl.$^7$ .......................... C12P 21/06; C12N 15/00; C12N 5/10; C12N 7/01

[52] U.S. Cl. ..................... 435/325; 435/69.1; 435/91.1; 435/91.41; 435/366; 435/320.1; 435/235.1; 424/199.1; 514/44; 536/23.72; 536/24.1

[58] Field of Search .................... 435/69.1, 91.1, 435/91.41, 172.3, 172.1, 235.1, 325, 366, 320.1; 424/199.1; 514/44; 536/23.72, 24.1

[56] References Cited

FOREIGN PATENT DOCUMENTS

| | | |
|---|---|---|
| 2 707 664 | 1/1995 | France . |
| 94/12649 | 6/1994 | WIPO . |
| 94/28152 | 12/1994 | WIPO . |
| 95/02697 | 1/1995 | WIPO . |
| 95/06743 | 3/1995 | WIPO . |
| 95/20671 | 3/1995 | WIPO . |
| 95/23867 | 8/1995 | WIPO . |

OTHER PUBLICATIONS

Ferrari et al., Second–Strand Synthesis Is a Rate–Limiting Step for Efficient Transduction by Recombinant Adeno–Associated Virus Vectors, Journal of Virology 70(5), 3227–3234 (1996).
Ko et al., A Highly Inducible System of Gene Expression by Positive Feedback Production of Glucocorticoid Receptors, DNA 8(2) 127–133 (1989).
Ketner et al., Complementation of adenovirus E4 mutants by transient expression of E4 cDNA and deletion plasmids, Nucleic Acids Research 17, 3037–3048 (1989).
Ohman et al., Two Adenovirus Proteins with Redundant Activities in Virus Growth Facilitates Tripartite Leader mRNA Accumulation, Virology 194, 50–58 (1993).
Ohman et al., Effect of adenovirus–2 early r egion 4 products on E1 transformation, International Journal of Oncology 6, 663–668 (1995).
Bridge et al., Adenovirus Early Region 4 and Viral DNA Synthesis, Virology 193, 794–801 (1983).
Weinberg et al., Adenoviral Early Region 4 Is Required for Efficient Viral DNA Replication and for Late Gene Expression, Journal of Virology 57(3) 833–838 (1986).
Bridge et al., Redundant Control of Adenovirus Late Gene Expression by Early Region 4, Journal of Virology 63(2), 631–638 (1989).
Weinberg et al., A cell line that supports the growth of a defective early region 4 deletion mutant of human adenovirus type 2, Proc. Natl. Acad. Sci. 80, 5383–5386 (1983).
Kremer et al., Adenovirus and adeno–associated virus mediated gene transfer, British Medical Bulletin 51(1) 31–44 (1995).
Rolling et al., AAV as a Viral Vector for Human Gene Therapy, Molecular Biotechnology 3(1) 9–15 (1995).
Hemstrom et al., Adenovirus E4–Dependent Activation of the Early E2 Promoter Is Insufficient To Promote the Early–to–Late–Phase Transition, Journal of Virology 65(3), 1440–1449 (1991).
Yeh et al., Efficient Dual Transcomplementation of Adenovirus E1 and E4 Regions from a 293–Derived Cell Line Expressing a Minimal E4 Functional Unit, Journal of Virology 70(1) 559–565 (1996).

*Primary Examiner*—Mary E. Mosher
*Assistant Examiner*—Ali R. Salimi

[57] ABSTRACT

The invention relates to cells usable for the production of defective adenoviruses comprising, inserted into their genome, a portion of the region E4 of an adenovirus genome carrying the reading phase ORF6 under the control of a functional promoter.

33 Claims, 7 Drawing Sheets

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide"

(xi) SEQUENCE DESCRIPTION: SEQ ID NO:1:

AAGCAGCCAA GGGGTTGTTT 20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Oligonucleotide"

(xi) SEQUENCE DESCRIPTION: SEQ ID NO:2:

ACCCTAGTAT TCAACCTGCC 20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
            (A) DESCRIPTION: /desc = "Oligonucleotide"

(xi) SEQUENCE DESCRIPTION: SEQ ID NO:3:

ATCATCACAA GAGCGGAACG                                                       20

(2) INFORMATION FOR SEQ ID NO:4:

(i) SEQUENCE CHARACTERISTICS:
            (A) LENGTH: 3189 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:4:

CATCCTCTTA CACTTTTTCA TACATTGCCC AAGAATAAAG AATCGTTTGT GTTATGTTTC        60

AACGTGTTTA TTTTTCAATT GCAGAAAATT TCAAGTCATT TTTCATTCAG TAGTATAGCC       120

CCACCACCAC ATAGCTTATA CAGATCACCG TACCTTAATC AAACTCACAG AACCCTAGTA       180

TTCAACCTGC CACCTCCCTC CCAACACACA GAGTACACAG TCCTTTCTCC CCGGCTGGCC       240

TTAAAAAGCA TCATATCATG GGTAACAGAC ATATTCTTAG GTGTTATATT CCACACGGTT       300

TCCTGTCGAG CCAAACGCTC ATCAGTGATA TTAATAAACT CCCCGGGCAG CTCACTTAAG       360

TTCATGTCGC TGTCCAGCTG CTGAGCCACA GGCTGCTGTC CAACTTGCGG TTGCTTAACG       420

GGCGGCGAAG GAGAAGTCCA CGCCTACATG GGGGTAGAGT CATAATCGTG CATCAGGATA       480

GGGCGGTGGT GCTGCAGCAG CGCGCGAATA AACTGCTGCC GCCGCCGCTC CGTCCTGCAG       540

GAATACAACA TGGCAGTGGT CTCCTCAGCG ATGATTCGCA CCGCCCGCAG CATAAGGCGC       600

CTTGTCCTCC GGGCACAGCA GCGCACCCTG ATCTCACTTA AATCAGCACA GTAACTGCAG       660

CACAGCACCA CAATATTGTT CAAAATCCCA CAGTGCAAGG CGCTGTATCC AAAGCTCATG       720

GCGGGGACCA CAGAACCCAC GTGGCCATCA TACCACAAGC GCAGGTAGAT TAAGTGGCGA       780

CCCCTCATAA ACACGCTGGA CATAAACATT ACCTCTTTTG GCATGTTGTA ATTCACCACC       840

TCCCGGTACC ATATAAACCT CTGATTAAAC ATGGCGCCAT CCACCACCAT CCTAAACCAG       900

CTGGCCAAAA CCTGCCCGCC GGCTATACAC TGCAGGGAAC CGGGACTGGA ACAATGACAG       960

TGGAGAGCCC AGGACTCGTA ACCATGGATC ATCATGCTCG TCATGATATC AATGTTGGCA      1020

CAACACAGGC ACACGTGCAT ACACTTCCTC AGGATTACAA GCTCCTCCCG CGTTAGAACC      1080

ATATCCCAGG GAACAACCCA TTCCTGAATC AGCGTAAATC CCACACTGCA GGGAAGACCT      1140

CGCACGTAAC TCACGTTGTG CATTGTCAAA GTGTTACATT CGGGCAGCAG CGGATGATCC      1200

TCCAGTATGG TAGCGCGGGT TTCTGTCTCA AAAGGAGGTA GACGATCCCT ACTGTACGGA      1260

GTGCGCCGAG ACAACCGAGA TCGTGTTGGT CGTAGTGTCA TGCCAAATGG AACGCCGGAC      1320

GTAGTCATAT TTCCTGAAGC AAAACCAGGT GCGGGCGTGA CAAACAGATC TGCGTCTCCG      1380

GTCTCGCCGC TTAGATCGCT CTGTGTAGTA GTTGTAGTAT ATCCACTCTC TCAAAGCATC      1440

CAGGCGCCCC CTGGCTTCGG GTTCTATGTA AACTCCTTCA TGCGCCGCTG CCCTGATAAC      1500

ATCCACCACC GCAGAATAAG CCACACCCAG CCAACCTACA CATTCGTTCT GCGAGTCACA      1560

CACGGGAGGA GCGGGAAGAG CTGGAAGAAC CATGTTTTTT TTTTTATTCC AAAAGATTAT      1620

CCAAAACCTC AAAATGAAGA TCTATTAAGT GAACGCGCTC CCCTCCGGTG GCGTGGTCAA      1680

ACTCTACAGC CAAAGAACAG ATAATGGCAT TTGTAAGATG TTGCACAATG GCTTCCAAAA      1740

```
GGCAAACGGC CCTCACGTCC AAGTGGACGT AAAGGCTAAA CCCTTCAGGG TGAATCTCCT    1800

CTATAAACAT TCCAGCACCT TCAACCATGC CCAAATAATT CTCATCTCGC CACCTTCTCA    1860

ATATATCTCT AAGCAAATCC CGAATATTAA GTCCGGCCAT TGTAAAAATC TGCTCCAGAG    1920

CGCCCTCCAC CTTCAGCCTC AAGCAGCGAA TCATGATTGC AAAAATTCAG GTTCCTCACA    1980

GACCTGTATA AGATTCAAAA GCGGAACATT AACAAAAATA CCGCGATCCC GTAGGTCCCT    2040

TCGCAGGGCC AGCTGAACAT AATCGTGCAG GTCTGCACGG ACCAGCGCGG CCACTTCCCC    2100

GCCAGGAACC ATGACAAAAG AACCCACACT GATTATGACA CGCATACTCG GAGCTATGCT    2160

AACCAGCGTA GCCCCGATGT AAGCTTGTTG CATGGGCGGC GATATAAAAT GCAAGGTGCT    2220

GCTCAAAAAA TCAGGCAAAG CCTCGCGCAA AAAGAAAGC ACATCGTAGT CATGCTCATG     2280

CAGATAAAGG CAGGTAAGCT CCGGAACCAC CACAGAAAAA GACACCATTT TTCTCTCAAA    2340

CATGTCTGCG GGTTTCTGCA TAAACACAAA ATAAAATAAC AAAAAAACAT TTAAACATTA    2400

GAAGCCTGTC TTACAACAGG AAAAACAACC CTTATAAGCA TAAGACGGAC TACGGCCATG    2460

CCGGCGTGAC CGTAAAAAAA CTGGTCACCG TGATTAAAAA GCACCACCGA CAGCTCCTCG    2520

GTCATGTCCG GAGTCATAAT GTAAGACTCG GTAAACACAT CAGGTTGATT CACATCGGTC    2580

AGTGCTAAAA AGCGACCGAA ATAGCCCGGG GGAATACATA CCCGCAGGCG TAGAGACAAC    2640

ATTACAGCCC CCATAGGAGG TATAACAAAA TTAATAGGAG AGAAAACAC ATAAACACCT     2700

GAAAAACCCT CCTGCCTAGG CAAAATAGCA CCCTCCCGCT CCAGAACAAC ATACAGCGCT    2760

TCCACAGCGG CAGCCATAAC AGTCAGCCTT ACCAGTAAAA AAGAAAACCT ATTAAAAAAA    2820

CACCACTCGA CACGGCACCA GCTCAATCAG TCACAGTGTA AAAAAGGGCC AAGTGCAGAG    2880

CGAGTATATA TAGGACTAAA AAATGACGTA ACGGTTAAAG TCCACAAAAA ACACCCAGAA    2940

AACCGCACGC GAACCTACGC CCAGAAACGA AAGCCAAAAA ACCCACAACT TCCTCAAATC    3000

GTCACTTCCG TTTTCCCACG TTACGTCACT TCCCATTTTA AGAAAACTAC AATTCCCAAC    3060

ACATACAAGT TACTCCGCCC TAAAACCTAC GTCACCCGCC CCGTTCCCAC GCCCCGCGCC    3120

ACGTCACAAA CTCCACCCCC TCATTATCAT ATTGGCTTCA ATCCAAAATA AGGTATATTA    3180

TTGATGATG                                                           3189

(2) INFORMATION FOR SEQ ID NO:5:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:5:

GGGCCCGCCG CCACCATGGA TATTGAACCT GAAGTGTTAT ATGCAGGA                 48

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:6:
```

-continued

```
CTCGAGAACG CCGGACGTAG TCTTTTGATG AAACAGAAG                         39
```

(2) INFORMATION FOR SEQ ID NO:7:

(i) SEQUENCE CHARACTERISTICS:
        (A) LENGTH: 1884 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

```
ATGGATATTG AACCTGAAGT GTTATATGCA GGATATGATA GCTCTGTTCC AGACTCAACT    60
TGGAGGATCA TGACTACGCT CAACATGTTA GGAGGGCGGC AAGTGATTGC AGCAGTGAAA   120
TGGGCAAAGG CAATACCAGG TTTCAGGAAC TTACACCTGG ATGACCAAAT GACCCTACTG   180
CAGTACTCCT GGATGTTTCT TATGGCATTT GCTCTGGGGT GGAGATCATA TAGACAATCA   240
AGTGCAAACC TGCTGTGTTT TGCTCCTGAT CTGATTATTA TGAGCAGAG AATGACTCTA    300
CCCTGCATGT ACGACCAATG TAAACACATG CTGTATGTTT CCTCTGAGTT ACACAGGCTT   360
CAGGTATCTT ATGAAGAGTA TCTCTGTATG AAAACCTTAC TGCTTCTCTC TTCAGTTCCT   420
AAGGACGGTC TGAAGAGCCA AGAGCTATTT GATGAAATTA GAATGACCTA CATCAAAGAG   480
CTAGGAAAAG CCATTGTCAA GAGGGAAGGA AACTCCAGCC AGAACTGGCA GCGGTTTTAT   540
CAACTGACAA AACTCTTGGA TTCTATGCAT GAAGTGGTTG AAAATCTCCT TAACTATTGC   600
TTCCAAACAT TTTTGGATAA GACCATGAGT ATTGAATTCC CCGAGATGTT AGCTGAAATC   660
ATCACCAATC AGATACCAAA ATATTCAAAT GGAAATATCA AAAAACTTCT GTTTCATCAA   720
AAGACTACGT CCGGCGTTCC ATTTGGCATG ACACTACGAC CAACACGATC TCGGTTGTCT   780
CGGCGCACTC CGTACAGTAG GGATCGTCTA CCTCCTTTTG AGACAGAAAC CCGCGCTACC   840
ATACTGGAGG ATCATCCGCT GCTGCCCGAA TGTAACACTT TGACAATGCA AACGTGAGT    900
TACGTGCGAG GTCTTCCCTG CAGTGTGGGA TTTACGCTGA TTCAGGAATG GGTTGTTCCC   960
TGGGATATGG TTCTAACGCG GGAGGAGCTT GTAATCCTGA GGAAGTGTAT GCACGTGTGC  1020
CTGTGTTGTG CCAACATTGA TATCATGACG AGCATGATGA TCCATGGTTA CGAGTCCTGG  1080
GCTCTCCACT GTCATTGTTC CAGTCCCGGT TCCCTGCAGT GTATAGCCGG CGGGCAGGTT  1140
TTGGCCAGCT GGTTTAGGAT GGTGGTGGAT GGCGCCATGT TTAATCAGAG GTTTATATGG  1200
TACCGGGAGG TGGTGAATTA CAACATGCCA AAAGAGGTAA TGTTTATGTC CAGCGTGTTT  1260
ATGAGGGGTC GCCACTTAAT CTACCTGCGC TTGTGGTATG ATGGCCACGT GGGTTCTGTG  1320
GTCCCCGCCA TGAGCTTTGG ATACAGCGCC TTGCACTGTG GGATTTTGAA CAATATTGTG  1380
GTGCTGTGCT GCAGTTACTG TGCTGATTTA AGTGAGATCA GGGTGCGCTG CTGTGCCCGG  1440
AGGACAAGGC GCCTTATGCT GCGGGCGGTG CGAATCATCG CTGAGGAGAC CACTGCCATG  1500
TTGTATTCCT GCAGGACGGA GCGGCGGCGG CAGCAGTTTA TTCGCGCGCT GCTGCAGCAC  1560
CACCGCCCTA TCCTGATGCA CGATTATGAC TCTACCCCCA TGTAGGCGTG GACTTCTCCT  1620
TCGCCGCCCG TTAAGCAACC GCAAGTTGGA CAGCAGCCTG TGGCTCAGCA GCTGGACAGC  1680
GACATGAACT TAAGTGAGCT GCCCGGGGAG TTTATTAATA TCACTGATGA GCGTTTGGCT  1740
CGACAGGAAA CCGTGTGGAA TATAACACCT AAGAATATGT CTGTTACCCA TGATATGATG  1800
CTTTTTAAGG CCAGCCGGGG AGAAAGGACT GTGTACTCTG TGTGTTGGGA GGGAGGTGGC  1860
AGGTTGAATA CTAGGGTTCT GTGA                                        1884
```

(2) INFORMATION FOR SEQ ID NO:8:

(i) SEQUENCE CHARACTERISTICS:
        (A) LENGTH: 534 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Met Asp Ile Glu Pro Glu Val Leu Tyr Ala Gly Tyr Asp Ser Ser Val
 1               5                  10                  15

Pro Asp Ser Thr Trp Arg Ile Met Thr Thr Leu Asn Met Leu Gly Gly
                20                  25                  30

Arg Gln Val Ile Ala Ala Val Lys Trp Ala Lys Ala Ile Pro Gly Phe
            35                  40                  45

Arg Asn Leu His Leu Asp Asp Gln Met Thr Leu Leu Gln Tyr Ser Trp
 50                  55                  60

Met Phe Leu Met Ala Phe Ala Leu Gly Trp Arg Ser Tyr Arg Gln Ser
 65                  70                  75                  80

Ser Ala Asn Leu Leu Cys Phe Ala Pro Asp Leu Ile Ile Asn Glu Gln
                85                  90                  95

Arg Met Thr Leu Pro Cys Met Tyr Asp Gln Cys Lys His Met Leu Tyr
            100                 105                 110

Val Ser Ser Glu Leu His Arg Leu Gln Val Ser Tyr Glu Glu Tyr Leu
        115                 120                 125

Cys Met Lys Thr Leu Leu Leu Leu Ser Ser Val Pro Lys Asp Gly Leu
130                 135                 140

Lys Ser Gln Glu Leu Phe Asp Glu Ile Arg Met Thr Tyr Ile Lys Glu
145                 150                 155                 160

Leu Gly Lys Ala Ile Val Lys Arg Glu Gly Asn Ser Ser Gln Asn Trp
                165                 170                 175

Gln Arg Phe Tyr Gln Leu Thr Lys Leu Leu Asp Ser Met His Glu Val
            180                 185                 190

Val Glu Asn Leu Leu Asn Tyr Cys Phe Gln Thr Phe Leu Asp Lys Thr
        195                 200                 205

Met Ser Ile Glu Phe Pro Glu Met Leu Ala Glu Ile Ile Thr Asn Gln
210                 215                 220

Ile Pro Lys Tyr Ser Asn Gly Asn Ile Lys Lys Leu Leu Phe His Gln
225                 230                 235                 240

Lys Thr Thr Ser Gly Val Pro Phe Gly Met Thr Leu Arg Pro Thr Arg
                245                 250                 255

Ser Arg Leu Ser Arg Arg Thr Pro Tyr Ser Arg Asp Arg Leu Pro Pro
            260                 265                 270

Phe Glu Thr Glu Thr Arg Ala Thr Ile Leu Glu Asp His Pro Leu Leu
        275                 280                 285

Pro Glu Cys Asn Thr Leu Thr Met His Asn Val Ser Tyr Val Arg Gly
290                 295                 300

Leu Pro Cys Ser Val Gly Phe Thr Leu Ile Gln Glu Trp Val Val Pro
305                 310                 315                 320

Trp Asp Met Val Leu Thr Arg Glu Glu Leu Val Ile Leu Arg Lys Cys
                325                 330                 335

Met His Val Cys Leu Cys Cys Ala Asn Ile Asp Ile Met Thr Ser Met
            340                 345                 350
```

-continued

```
Met Ile His Gly Tyr Glu Ser Trp Ala Leu His Cys His Cys Ser Ser
        355                 360                 365
Pro Gly Ser Leu Gln Cys Ile Ala Gly Gly Gln Val Leu Ala Ser Trp
        370                 375                 380
Phe Arg Met Val Val Asp Gly Ala Met Phe Asn Gln Arg Phe Ile Trp
385                     390                 395                 400
Tyr Arg Glu Val Val Asn Tyr Asn Met Pro Lys Glu Val Met Phe Met
                405                 410                 415
Ser Ser Val Phe Met Arg Gly Arg His Leu Ile Tyr Leu Arg Leu Trp
                420                 425                 430
Tyr Asp Gly His Val Gly Ser Val Val Pro Ala Met Ser Phe Gly Tyr
            435                 440                 445
Ser Ala Leu His Cys Gly Ile Leu Asn Asn Ile Val Val Leu Cys Cys
        450                 455                 460
Ser Tyr Cys Ala Asp Leu Ser Glu Ile Arg Val Arg Cys Cys Ala Arg
465                     470                 475                 480
Arg Thr Arg Arg Leu Met Leu Arg Ala Val Arg Ile Ile Ala Glu Glu
                485                 490                 495
Thr Thr Ala Met Leu Tyr Ser Cys Arg Thr Glu Arg Arg Arg Gln Gln
                500                 505                 510
Phe Ile Arg Ala Leu Leu Gln His His Arg Pro Ile Leu Met His Asp
        515                 520                 525
Tyr Asp Ser Thr Pro Met
        530
```

CELLS FOR THE PRODUCTION OF RECOMBINANT ADENOVIRUSES

The present invention relates to new cell lines which can be used for the production of defective recombinant adenoviruses. It also relates to the purified viral preparations produced in these lines, as well as the plasmids allowing their construction. More particularly, the new cell lines according to the invention allow the transcomplementation of the E4 region and a clonal production with high titers of defective recombinant adenoviruses especially for all or part of the E4 region.

Adenoviruses exhibit certain properties which are particularly advantageous for use as vector for the transfer of genes in gene therapy. In particular, they have a fairly broad host spectrum, are capable of infecting quiescent cells, do not integrate into the genome of the infected cell, and have not been associated, up until now, with major pathologies in man. Adenoviruses have thus been used to transfer genes of interest into the muscle (Ragot et al., Nature 361 (1993) 647), the liver (Jaffe et al., Nature genetics 1 (1992) 372), the nervous system (Akli et al., Nature genetics 3 (1993) 224), and the like.

Adenoviruses are viruses with a linear double-stranded DNA having a size of about 36 kb. Their genome comprises especially an inverted repeat sequence (ITR) at each end, an encapsidation sequence (Psi), early genes and late genes (Cf. FIG. 1). The principal early genes are contained in the E1, E2, E3 and E4 regions. Among these, the genes contained in the E1 region in particular are necessary for viral propagation. The principal late genes are contained in the L1 to L5 regions. The genome of the Ad5 adenovirus has been completely sequenced and is accessible on a database (see especially Genebank M73260). Likewise, parts or even the whole of other adenoviral genomes (Ad2, Ad7, Ad12 and the like) have also been sequenced.

For their use in gene therapy, various vectors derived from adenoviruses have been prepared, incorporating various genes (β-gal, OTC, α-1AT, cytokines and the like). In each of these constructs, the adenovirus was modified so as to render it incapable of replicating in the infected cell. Thus, the constructs described in the prior art are adenoviruses from which the E1 region has been deleted, which region is essential for the viral replication and at the level of which the heterologous DNA sequences are inserted (Levrero et al., Gene 101 (1991) 195; Gosh-Choudhury et al., Gene 50 (1986) 161). These adenoviruses are produced in a complementation line (line 293) into which part of the adenovirus genome has been integrated. More precisely, line 293 contains the left end (about 11–12%) of the serotype 5 adenovirus (Ad5) genome comprising the left ITR, the encapsidation region, the E1 region, including E1a, E1b, the region encoding the pIX protein and part of the region encoding the pIVa2 protein. This line is capable of trans-complementing recombinant adenoviruses defective for the E1 region, that is to say lacking all or part of the E1 region, and of producing viral stocks having high titers. However, vectors deficient for the E1 region (E1⁻ vectors, termed first generation vectors) exhibit certain disadvantages for a therapeutic use. In particular, they might not be completely defective for in vivo replication especially because of the existence of certain transcomplementing cellular functions. Thus, an E1 transcomplementation activity has been detected in F9 embryonic carcinoma cells (Imperiale et al., Mol. Cell. Biol. 4, 1984, 867–874). An activity of the same type, regulated by interleukin-6, has also been detected (Spergel et al., J. Virol. 66, 1992, 1021–1030). Other disadvantages linked to these vectors are the presence of numerous viral genes, capable of being expressed in vivo after gene transfer, and of inducing an immune and/or inflammatory response.

In order to overcome these disadvantages, it has been proposed to create other deletions or modifications in the adenovirus genome. Thus, a heat-sensitive point mutation has been introduced into the ts125 mutant, making it possible to inactivate the 72 kDa DNA binding protein (DBP) (Van der Vliet et Sussenbach, Virology 67, 1975, 415–426). These vectors can also be produced with high titers in the cells of the 293 line at the permissive temperature (32° C.). However, this type of vector also has a number of disadvantages such as an overexpression in vivo of the E4 region, the presence of a point mutation which is therefore subject to reversion, a risk of partial activity at 37° C., and the like.

Another approach for overcoming these problems lies in the deletion of another region essential for viral replication and/or propagation. In this regard, the applicant was more particularly interested in the E4 region. The E4 region is indeed involved in the regulation of the expression of the late genes, in the stability of the late nuclear RNAs, in the extinction of the expression of the host cell proteins and in the efficacy of the replication of the viral DNA. Adenoviral vectors in which the E1 and E4 regions are deleted therefore possess a transcription background noise and an expression of viral genes which are very reduced (see especially the application PCT/FR94/00851). However, the construction and industrial and therapeutic exploitation of such vectors requires the availability of an efficient system for the transcomplementation of these two functions for the production of viral stocks.

The present invention offers a solution to this problem. The present invention indeed provides cell lines which allow the transcomplementation of the E4 region and a clonal production and with high titers of recombinant adenoviruses defective for this region. The lines according to the invention are advantageously capable of transcomplementing the two E1 and E4 functions and therefore make it possible to produce viruses deficient for these two functions. The present invention also provides plasmids which allow the construction of these lines, a process for the preparation of defective recombinant adenoviruses and purified viral stocks. More particularly, the applicant has now shown that producing lines capable of efficiently transcomplementing the E4 region are obtained by the introduction of only part of the E4 region. Thus, lines having particularly advantageous properties are obtained when only a small functional unit of the E4 region, corresponding to the reading frame ORF6 or to the reading frames ORF6 and ORF6/7, is present.

A first subject of the invention therefore consists in a cell which can be used for the production of defective recombinant adenoviruses comprising, inserted into its genome, part of the E4 region of an adenovirus genome containing the reading frame ORF6 under the control of a functional promoter. According to a preferred mode, the cells of the invention comprise part of the E4 region of an adenovirus genome containing the reading frames ORF6 and ORF6/7 under the control of a functional promoter.

As indicated above, the cell lines according to the present invention exhibit particularly advantageous properties: they allow, first of all, the transcomplementation of the E1 and E4 functions. However, in a particularly advantageous manner, they are capable of inducing the formation of plaques of viruses deficient in these functions, which is essential for the cloning of recombinant viruses and for their amplification and their purification. In this regard, the applicant has indeed shown that lines possessing the entire E4 region or larger functional units, including for example the reading frame ORF4, are incapable of forming plaques of viruses deficient for the E4 region. The identification of specific functional units of the E4 region allows the production of a very efficient system for the transcomplementation and production of viruses defective for the E1 and E4 functions. Other advantages of the lines according to the invention are especially their capacity for the amplification in liquid medium of such viruses deficient for the E1 and E4 regions, the high titers of such viruses which they produce, and the absence of production of a contaminant replicative viral particle.

Figure 2:
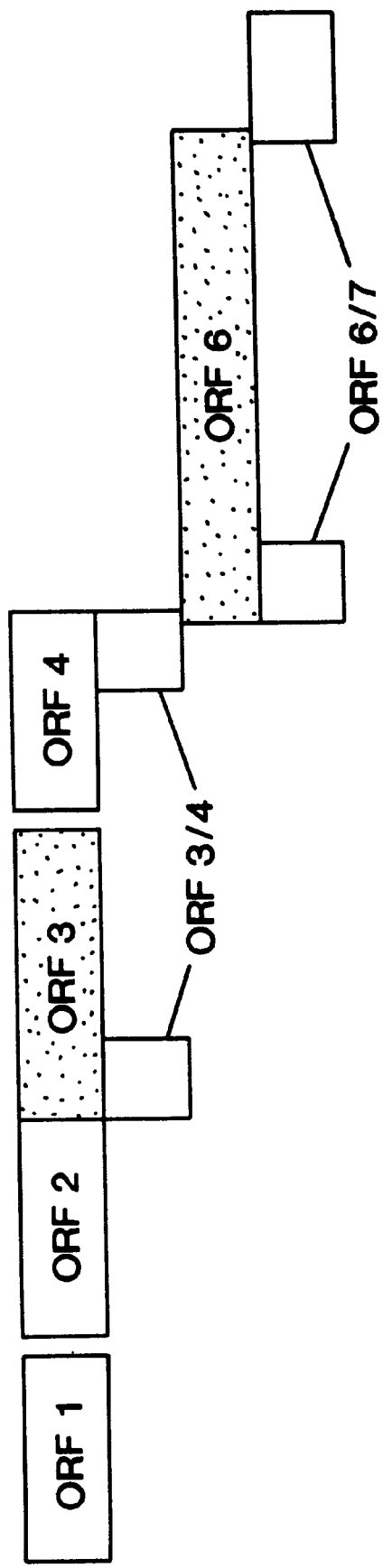
Figure 3:
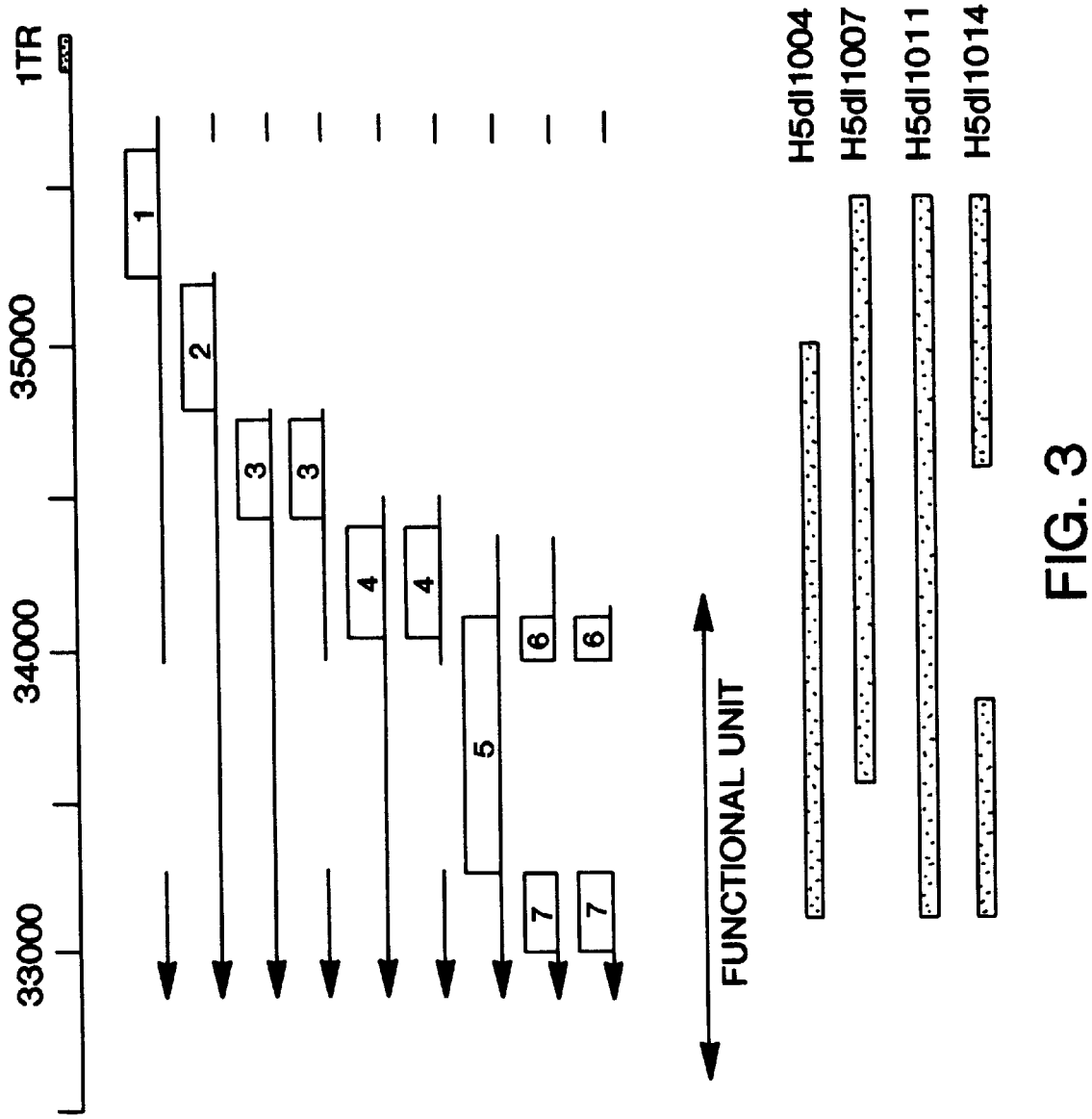

The E4 region of the adenoviral genome consists of 7 open reading frames designated ORF1, ORF2, ORF3, ORF4, ORF3/4, ORF6 and ORF6/7 (FIGS. 2 and 3). As indicated above, the cells of the invention are particularly characterized by the presence of only part of this region, comprising the reading frame ORF6 optionally combined with the reading frame ORF6/7. It is particularly important that the part of the E4 region present in the cells of the invention does not contain the functional ORF4 reading frame. Advantageously, the E4 region present in the cells of the invention does not contain the functional ORF1–ORF4 reading frames. In a particularly preferred manner, at least part of the ORF1–ORF4 reading frames is deleted from the E4 region present in the cells of the invention. These different parts of the E4 region can be obtained by enzymatic cleavages or modified according to methods known to persons skilled in the art. According to a preferred embodiment, the cell lines of the invention comprise an inserted fragment containing less than 2 kb of the E4 region of an adenovirus genome containing the whole of the reading frames ORF6 and optionally ORF6/7. By way of preferred examples, the reading frame ORF6 can be isolated from the E4 region in the form of a BglII-PvuII fragment, corresponding to nucleotides 34115–33126, and the reading frames ORF6–ORF6/7 can be isolated from the E4 region in the form of a BglII-BglII fragment corresponding to nucleotides 34115–32490 of the Ad5 genome. According to a specific embodiment of the invention, the reading frame (ORF6) is fused in translational phase with the domain of a nuclear receptor which is responsible for recognizing its specific ligand. The hormone-binding domain (HBD) of the glucocorticoid receptor (GCR: Hollenberg et al. 1985, Nature, 318, 635–341) is advantageously chosen because it makes it possible to retain, in the cytoplasmic compartment of the cell, the fusion protein in the absence of hormone (T. MATTIONI et al., 1994, Methods in Cell Biology, Chapter 16, 335–352) by virtue of the stable interaction of HBD (GCR) with the cytoplasmic protein hsp90 and other cofactors (S. P. BOHEN et al., 1995, Science, 268, 1303–1304). The presence of the hormone then causes the translocation of the fusion protein from the cytoplasm to the nucleus, which allows the functionality of the ORF6 activity of E4 in the nuclear compartment. It is also possible that the addition of hormone causes "unmasking" of the functional domains of the ORF6 activity by a transconformational change in the hybrid protein.

In this regard, a particularly preferred embodiment of the invention consists of a cell comprising, inserted into its genome, a BglII-BglII fragment corresponding to nucleotides 34115–32490 of the Ad5 genome. This fragment is present especially in the plasmid pORF6Gen described in the examples, which is used for the construction of the cell line clone#2. Another particularly preferred embodiment of the invention consists of a cell comprising, inserted into its genome, a BglII-PvuII fragment corresponding to nucleotides 34115–33126 of the Ad5 genome. In another embodiment of the invention, at least the ORF6 region is coupled to the HBD of the GCR, either at its C-terminal end (GCR-ORF6 fusion), or at its N-terminal end (ORF6-GCR fusion). In the case of the C-terminal fusion, the sequence from the virus encoding ORF6 and ORF7 is advantageously inserted in translational phase downstream of the sequence specifying the HBD of the GCR. In this specific embodiment, the expression of the chimeric gene then generates a primary RNA whose translational product is the GCR-ORF6 protein (SEQ ID No. 7). Alternate splicing of this transcript generates, for its part, a messenger RNA which encodes the fusion protein GCR-ORF6/7 (cf. Example 1.5).

The part of the E4 region present in the cells according to the invention may be derived from adenoviruses of different origins or serotypes. There are indeed various adenovirus serotypes, whose structure and properties can vary somewhat, but which exhibit a comparable genetic organization. More particularly, the E4 region present in the cells according to the invention may be derived from an adenovirus of human or animal origin.

As regards adenoviruses of human origin, there may be mentioned preferably those classified in group C. Still more preferably, among the various human adenovirus serotypes, the use of the type 2 or 5 adenoviruses (Ad2 or Ad5) is preferred within the framework of the present invention. Among the various adenoviruses of animal origin, the use of adenoviruses of canine origin, and especially all the strains of the CAV2 adenoviruses [manhattan strain or A26/61 (ATCC VR-800) for example] is preferred within the framework of the invention. Other adenoviruses of animal origin are mentioned especially in the application WO94/26914 incorporated into the present by way of reference.

In a preferred embodiment of the invention, the part of the E4 region is derived from a group C human adenovirus genome. More preferably, it is derived from the genome of an Ad2 or Ad5 adenovirus.

As indicated above, the part of the E4 region present in the cells of the invention is placed under the control of a promoter which is functional in the said cells. Advantageously, this is an inducible promoter which makes it possible to control the levels and/or periods of expression of these genes. In a particularly advantageous manner, it is the MMTV LTR promoter (Pharmacia) which is induced by dexamethasone or it is a promoter which is regulated by tetracycline (WO94/29442; WO94/04672). It is understood that other promoters can be used, and especially variants of the MMTV LTR carrying for example heterologous regulatory regions (especially enhancer regions).

In a specific embodiment, the expression of the hybrid genes is under the control of regulated promoters so as to avoid constitutive accumulation of the fusion protein in the cytoplasm, or to minimize "leakage" to the nuclear compartment and a degree of cytotoxicity. In a still more specific embodiment, the chimeric gene is under the control of an inducible promoter which responds to glucocorticoids such as the GRE5 promoter (S. Mader and J. White, 1993, PNAS, 90, 5603–5607: cf. Example 1.5).

The cells according to the invention can be prepared from various cells which can be used pharmaceutically, that is to say which can be cultivated under industrially acceptable conditions and having no acknowledged pathogenic character. They may be established cell lines or primary cultures and especially human embryonic retina cells. They are advantageously cells of human origin which are infectable by an adenovirus. In this regard, there may be mentioned the KB, Hela, 293, Vero and gmDBP6 cells and the like.

The cells of the KB line are derived from a human epidermal carcinoma. They are accessible at the ATCC (ref. CCL17) as well as the conditions allowing their culture. The human cell line Hela is derived from a human epithelium carcinoma. It is also accessible at the ATCC (ref. CCL2) as well as the conditions allowing its culture. The line 293 cells are human embryonic kidney cells (Graham et al., J. Gen. Virol. 36 (1977) 59). This line contains especially, integrated in its genome, the left part of the genome of the human adenovirus Ad5 (12%). The cell line gmDBP6 (Brough et al., Virology 190 (1992) 624) consists of Hela cells carrying the adenovirus E2 gene under the control of the MMTV LTR.

They may also be cells of canine origin (BHK, MDCK, and the like). In this regard, the cells of the canine line MDCK are preferred. The conditions for the culture of the MDCK cells have been described especially by Macatney et al., Science 44 (1988) 9.

The cell lines according to the invention can be constructed in various ways. In general, they are prepared by transformation of a cell culture with a plasmid carrying the fragment selected from the E4 region under the control of a functional promoter. The transfection of the cells can be carried out by any technique known to persons skilled in the art, and especially in the presence of calcium phosphate, by electroporation and the like. According to a specific embodiment, the plasmid used also carries a marker gene which makes it possible to identify and to select the transformed cells. This may be especially any gene for resistance to an antibiotic (geneticin, hygromycin and the like). The marker gene may also be carried by a separate construct, cotransfected with the plasmid. After transfection and selection for the marker gene, the cells obtained can be selected for their capacity to transcomplement adenoviruses lacking the E4 region. For that, various mutant adenoviruses defective for various parts of the E4 region can be used, such as especially the adenoviruses Ad2dl808 (Weinberg et Ketner, J. Virol. 57 (1986) 833), Ad5dl1004 dl1007 or dl1014 (Bridge et Ketner, J. Virol. 63 (1989) 631), dl1011 (Bridge et al., Virology 193 (1993) 794), as indicated in the examples.

Advantageously, the cells according to the invention are also capable of transcomplementing for the E1 region. These can be constructed as described above from cells which already transcomplement the E1 region (example: cells 293), or by sequential introduction of a construct providing the E1 region and of a construct providing the part of the E4 region according to the invention for example in retinoblasts of human origin.

According to a particularly preferred mode, the cells according to the invention are derived from the cell line 293. In this regard, particularly advantageous results have been obtained with cells of the line 293 which are transformed by the plasmid pORF6Gen or the plasmid pGGO which encodes the proteins HBD-ORF6 and HBD-ORF6/7.

The present invention also describes the construction of plasmids comprising part of the E4 region of an adenovirus genome carrying the reading frame ORF6 or ORF6 and ORF6/7 under the control of an inducible promoter (see especially the plasmids pORF6Gen and PGGO). These plasmids can be used directly to transfect a chosen cell population, and then, by selection, for the identification of cells which have stably acquired the E4 function.

Another subject of the invention consists in the use of the cells described above for the production of recombinant adenoviruses which are defective at least for the E4 region. The invention indeed provides a process for the production of particularly advantageous recombinant adenoviruses which are defective at least for the E4 region, using the cells above. According to this process, a culture of cells as described above is transformed with one or more plasmids providing the various regions of the genome of the said defective recombinant adenovirus and then the viruses produced are harvested. This process is particularly advantageous for the production of adenoviruses possessing the nonfunctional E1 and E4 regions. They are especially vectors in which the E1 and E4 regions have been inactivated or rendered nonfunctional by total or partial deletion. Such modifications can be obtained in vitro (on the isolated DNA) or in situ, for example, by means of genetic engineering techniques, or alternatively by treating with mutagenic agents. The said genetic modification(s) may be located in a coding part of the region, or outside a coding region, and for example in the regions responsible for the expression and/or transcriptional regulation of the said genes. The deletion may be performed by digesting with appropriate restriction enzymes, and then ligating, according to conventional molecular biology techniques.

According to a particularly advantageous mode, the process of the invention is used for the production of recombinant adenoviruses in which the E1 region is inactivated by deletion of a PvuII-BglII fragment stretching from nucleotide 454 to nucleotide 3328, in the Ad5 adenovirus sequence. This sequence is accessible in the literature and also on a database (see especially Genebank No. M73260). In another preferred embodiment, the E1 region is inactivated by deletion of an HinfII-Sau3A fragment stretching from nucleotide 382 to nucleotide 3446. In a specific mode, the process allows the production of vectors comprising a deletion of the whole of the E4 region. This may be carried out by excision of an MaeII-MscI fragment corresponding to nucleotides 35835–32720. The cell lines according to the invention are indeed capable of transcomplementing and of amplifying adenoviruses carrying any type of deletion or inactivation of the E4 region. In another specific mode, only a functional part of E4 is deleted. This part comprises at least the ORF3 and ORF6 frames. By way of example, these coding frames can be deleted from the genome in the form of PvuII-AluI and BglII-PvuII fragments respectively, corresponding to nucleotides 34801–34329 and 34115–33126 respectively. The deletions of the E4 region of the virus Ad2dl808 or of the viruses Ad5dl1004, Ad5dl1007, Ad5dl1011 or Ad5dl1014 can also be used within the framework of the invention. In this regard, the cells of the invention are particularly advantageous for the production of viruses comprising an inactive E1 region and a deletion in the E4 region of the type present in the genome of Ad5dl1014, that is to say of E4⁻ viruses conserving the reading frame ORF4.

The present invention therefore also describes defective recombinant adenoviruses whose genome comprises a deletion in the E1 region and a deletion in the E4 region. More particularly, it describes defective recombinant adenoviruses whose genome comprises a deletion in the E1 region and a deletion in the E4 region corresponding at least to the reading frames ORF3 and ORF6. Thus, the adenoviruses according to the invention preferably contain the following deletions which affect all or part of the E1 and E4 regions:

ΔE1,ORF3⁻,ORF6⁻ adenoviruses: deletion of all or part of the E1 region and of the nucleotides 34801–34329 and 34115–33126 of the E4 region;

ΔE1,ΔE4,ORF1⁺ adenoviruses: deletion of all or part of the E1 region and of the E4 region with the exception of the reading frame ORF1. This deletion in the E4 region covers preferably nucleotides 33093 (SmaI) to 35053 (AccIII). It is obtained for example from the mutant Ad5dl1004. Other deletions can be used for the production of ΔE1,ΔE4,ORF1⁺ adenoviruses of the invention, on the basis of the information given in the present application and of the nucleotide sequence SEQ ID No. 4. This double-stranded sequence represents the righthand part of the adenoviral genome, including the E4 region and the righthand ITR from nucleotide 32749 (1 on SEQ ID No. 4) to 35935 (3186 on SEQ ID No. 4). This is a purely illustrative sequence and other published sequences can also be used. The various reading frames of the E4 region are represented, especially ORF7, ORF6, ORF4, ORF3, ORF2 and ORF1. An ΔE1,ΔE4,ORF1⁺ adenovirus of the invention advantageously comprises a deletion in the E1 region and a deletion of a fragment whose 5' end is contained in the reading frame ORF7 and whose 3' end is situated in the reading frame ORF2. Still more preferably, the deletion relates to a fragment whose 5' end is between nucleotides 32920 and 33190 of the adenovirus genome and whose 3' end is between nucleotides 34710 and 35090 of the adenoviral genome. This deletion roughly corresponds to nucleotides 170 to 440 (5' end) and 1960 to 2340 (3' end) on the sequence SEQ ID No. 4.

ΔE1,ΔE4,ORF4⁺ adenoviruses: deletion of all or part of the E1 region and of the E4 region with the exception of the reading frame ORF4. An ΔE1,ΔE4,ORF4⁺ adenovirus of the invention advantageously comprises a deletion in the E1 region, a deletion of a fragment whose 5' end is contained in the reading frame ORF7 and whose 3' end is situated in the reading frame ORF6 (with the exception of the part overlapping the reading frame ORF4), and a deletion of a fragment whose 5' end is contained in the reading frame ORF3 and whose 3' end is situated in the reading frame ORF1 or in the promoter region of E4. More preferably, these adenoviruses according to the invention comprise:

(i) a deletion of all or part of E1, (ii) a deletion of a fragment whose 5' end is between nucleotides 32920 and 33190 of the adenovirus genome and whose 3' end is between nucleotides 33200 and 34000 of the adenoviral genome, and, (iii) a deletion of a fragment whose 5' end is between nucleotides 34360 and 34700 of the adenovirus genome and whose 3' end is between nucleotides 35150 and 35530 of the adenoviral genome.

The corresponding positions of the deletion (ii) on the sequence SEQ ID No. 4 are 180 to 445 (5' end) and 450 to 1250 (3' end). The corresponding positions of the deletion (iii) on the sequence SEQ ID No. 4 are 1610 to 1950 (5' end) and 2410 to 2870 (3' end).

These deletions in the E4 region cover preferably nucleotides 33093(SmaI)–33695 and 34634(SspI)–35355(SmaI). They can be obtained for example from the mutant Ad5dl1014.

ΔE1,ΔE4 adenoviruses: deletion of all or part of the E1 region and of nucleotides 32720–35835, or 33466–35355 (this deletion may be obtained for example from mutant Ad5dl1007) or 33093–35355 (this deletion may be obtained for example from the mutant Ad5dl1011). These 3 deletions cover the whole of the E4 region.

As indicated above, the deletion in the E1 region covers advantageously all or part of the E1A or E1B regions. This deletion should be sufficient to render the virus incapable of autonomous replication in a cell. The part of the E1 region which is deleted in the adenoviruses according to the invention advantageously covers nucleotides 454–3328 or 382–3446.

The positions given above refer to the wild-type Ad5 adenovirus sequence as published and accessible on a database. Although minor variations may exist between the various adenovirus serotypes, these positions are generally applicable to the construction of recombinant adenoviruses according to the invention from any serotype, and especially the adenoviruses Ad2 and Ad7.

Moreover, the adenoviruses of the invention may possess other alterations in their genome. In particular, other regions may be deleted in order to increase the capacity of the virus and reduce these side effects linked to the expression of viral genes. Thus, all or part of the E3 or IVa2 region in particular may be deleted. As regards the E3 region, it may however be particularly advantageous to conserve the part encoding the gp19K protein. This protein indeed makes it possible to prevent the adenovirus vector from becoming the subject of an immune reaction which (i) would limit its action and (ii) could have undesirable side effects. According to a specific mode, the E3 region is deleted and the sequence encoding the gp19K protein is reintroduced under the control of a heterologous promoter.

The recombinant adenoviruses according to the invention possess properties which are particularly attractive for use in gene therapy. These vectors indeed combine properties of infection, safety (the risks of immune and/or inflammatory reaction are highly reduced) and capacity to transfer genes which are very strong. Furthermore, the lines of the invention allow the production of viral stocks which are totally free of replicative contaminating particles (RCA). Thus, the results presented show the construction and the production, by the lines of the invention, of adenoviruses defective for the E1 and E4 regions, free of RCA. In particular, the appearance of E4⁺ replicative contaminating particles during the production of the ΔE1,ΔE4,ORF1⁺, ΔE1,ΔE4,ORF4⁺ or ΔE1,ΔE4 viruses according to the invention is not possible with the lines of the invention since (i) these viruses do not contain overlapping sequences on either side of the region integrated into the genome of the cell (FIG. 3) and (ii) a single homologous recombination event between the cellular and viral regions would generate a nonviable virus free of the righthand ITR. Another advantage of the viruses according to the invention consists in their increased cloning capacity which allows the insertion of large-sized transgenes (greater than 10 kb). This allows in particular the use of sequences which regulate transcription, making it possible to enhance the efficiency, the regulation and the duration of expression. This makes it possible, in addition, to use smaller doses of virus and to obtain a comparable therapeutic effect with very reduced cytopathic side effects.

As indicated above, adenoviruses constitute vectors for the transfer of genes which are very efficient for gene and cell therapy applications. For that, a heterologous nucleic acid sequence whose transfer and/or expression into a cell, an organ or an organism is desired may be inserted into their genome. This sequence may contain one or more therapeutic genes, such as a gene whose transcription and possible translation in the target cell generate products having a therapeutic effect. Among the therapeutic products, there may be mentioned more particularly enzymes, blood derivatives, hormones, lymphokines: interleukins, interferons, TNF and the like (FR 9203120), growth factors, neurotransmitters or their precursors or synthesis enzymes, trophic factors: BDNF, CNTF, NGF, IGF, GMF, aFGF, bFGF, NT3, NT5 and the like; apolipoproteins: ApoAI, ApoAIV, ApoE and the like (WO94/25073), dystrophin or a minidystrophin (WO93/06223), tumor suppressor genes: p53, Rb, Rap1A, DCC, k-rev and the like (WO94/24297), genes encoding factors involved in coagulation: factors VII, VIII, IX and the like, suicide genes: thymidine kinase, cytosine deaminase and the like, or alternatively all or part of a natural or artificial immunoglobulin (Fab, ScFv and the like, WO94/29446), and the like. The therapeutic gene may also be an antisense gene or sequence, whose expression in the target cell makes it possible to control the expression of genes or the transcription of cellular mRNAs. Such sequences can for example be transcribed, in the target cell, into RNAs which are complementary to cellular mRNAs and can thus block their translation into protein, according to the technique described in Patent EP 140 308. The therapeutic gene may also be a gene encoding an antigenic peptide, capable of generating an immune response in man, for the production of vaccines. They may be especially antigenic peptides specific for the Epstein-Barr virus, the HIV virus, the hepatitis B virus (EP 185 573), the pseudorabies virus, or specific for tumors (EP 259 212).

Generally, the heterologous nucleic acid sequence also comprises a transcription promoter region which is functional in the infected cell, as well as a region situated in 3' of the gene of interest, and which specifies a transcriptional end signal and a polyadenylation site. All of these elements constitute the expression cassette. As regards the promoter region, it may be a promoter region which is naturally responsible for the expression of the considered gene when the said promoter region is capable of functioning in the infected cell. It may also be regions of different origin (which are responsible for the expression of other proteins, or which are even synthetic). In particular, they may be promoter sequences of eukaryotic or viral genes or any promoter or derived sequence, stimulating or repressing the transcription of a gene in a specific manner or otherwise and in an inducible manner or otherwise. By way of example, they may be promoter sequences derived from the genome of the cell which it is desired to infect, or of the genome of a virus, especially the promoters of the adenovirus MLP, E1A genes, the RSV-LTR, CMV promoter, and the like. Among the eukaryotic promoters, there may also be mentioned the ubiquitous promoters (HPRT, vimentin, α-actin, tubilin and the like), the promoters of the intermediate filaments (desmin, neurofilaments, keratin, GFAP and the like), the promoters of therapeutic genes (MDR, CFTR, factor VIII type and the like), the tissue-specific promoters (pyruvate kinase, villin, the promoter for the intestinal fatty acid-binding protein, the promoter for α-actin of the smooth muscle cells, promoters specific for the liver; ApoAI, ApoAII, human albumin and the like) or alternatively the promoters which respond to a stimulus (steroid hormone receptor, retinoic acid receptor and the like). In addition these expression sequences may be modified by the addition of activating or regulatory sequences or of sequences allowing a tissue-specific or predominant expression. Moreover, when the inserted nucleic acid does not contain expression sequences, it may be inserted into the genome of the defective virus downstream of such a sequence.

Moreover, the heterologous nucleic acid sequence may also contain, in particular upstream of the therapeutic gene, a signal sequence directing the synthesized therapeutic product in the secretory pathways of the target cell. This signal sequence may be the natural signal sequence for the therapeutic product, but it may also be any other functional signal sequence or an artificial signal sequence.

The expression cassette for the therapeutic gene may be inserted into various sites of the genome of the recombinant adenovirus, according to the techniques described in the prior art. It can first of all be inserted at the level of the E1 deletion. It can also be inserted at the level of the E3 region, as an addition or as a substitution of sequences. It can also be located at the level of the deleted E4 region.

The cells according to the invention can also be used for the production of recombinant adeno-associated viruses (AAV). This constitutes another particularly advantageous application of the cells of the invention. These cells indeed make it possible to obtain high titers of rAAV, totally free of replicative contaminant viruses. In this regard, the present invention also relates to the use of a cell comprising, inserted into its genome, all or part of the E4 region of the genome of an adenovirus containing at least the reading frame ORF6 for the production of recombinant AAVs. The cells are advantageously as defined above.

AAV is a DNA virus of the human parvovirus family, of a relatively small size, which integrates into the genome of the cells which it infects, in a stable and site-specific manner. The AAVs are capable of infecting a broad spectrum of cells, without inducing any effect on the cell growth, morphology or differentiation. Moreover, they do not appear to be involved in pathologies in man. The genome of the AAVs has been cloned, sequenced and characterized. It comprises about 4700 bases and contains, at each end, an inverted repeat region (ITR) of about 145 bases which serves as replication origin for the virus. The remainder of the genome is divided into 2 essential regions carrying the encapsidation functions: the left part of the genome, which contains the rep gene involved in the viral replication and the expression of the viral genes; the right part of the genome, which contains the cap gene encoding the capsid proteins of the virus. The use of vectors derived from AAVs for the transfer of genes in vitro and in vivo has been described in the literature (see especially WO91/18088; WO93/09239; U.S. Pat. No. 4,797, 368, U.S. Pat. No. 5,139,941, EP 488 528). In the recombinant AAVs, the rep and cap genes are generally deleted and replaced by a gene of interest.

One of the difficulties limiting the use of AAVs as vector for gene therapy results from the fact that the AAV replicates efficiently only in cells co-infected with a helper virus such as for example the adenovirus or the herpes virus. The preparation of defective recombinant AAVs therefore requires the presence of 3 components which must be cotransfected and coinfected in the producing cell: a helper virus (for example an adenovirus), a plasmid containing a nucleic sequence of interest bordered by two AAV inverted repeat regions (ITR), and a plasmid carrying the AAV encapsidation genes (rep and cap genes).

The major disadvantage of this system is that it uses a helper virus. The latter is generally replicative and is present as a mixture with the rAAVs produced. The viral stocks are therefore potentially contaminated by a helper virus, thereby rendering these stocks incompatible with a therapeutic use. In addition, because of the large number of components involved in this process, the virus titers obtained are quite low, of the order of $10^8$.

The present invention makes it possible to overcome these disadvantages. The present invention indeed provides an efficient process for the production of rAAVs, which makes it possible to obtain virus stocks at very high titers (greater than $10^{10}$) which are not contaminated by a replicative virus.

Five adenovirus genes are necessary for the replication of the AAV: E1A, E1B, E2A, VA and E4. These genes must be present and expressed in the producing cell for an optimum production of infectious particles. According to the process of the invention, a producing cell line is now used which already contains, in its genome, some of these genes, and especially all or part of the E4 region, preferably combined with the E1 region. The benefit of using this type of cell line is that this makes it possible to use a defective helper adenovirus, that is to say which is not capable of autonomously generating infectious particles. Thus, the rAAV stocks produced are not contaminated.

Indeed, the functions integrated into the line can be deleted from the genome of the helper adenovirus.

This is particularly advantageous for using a helper adenovirus of human origin. Thus, in a cell line, as described above, which is capable of transcomplementing the E1 and E4 functions of the adenovirus, it is possible to use a helper adenovirus of human origin (Ad5 or Ad2 for example) which is defective for these functions. Such a helper adenovirus could not be efficiently used in the prior art processes because the absence of regions essential for the production of rAAVs (E1 and E4) considerably limited the efficiency of the process. Now, such an adenovirus is totally incapable of autonomously generating infectious particles. As a result, its possible presence in an rAAV stock does not affect the pharmaceutical quality of this preparation.

This also allows the more efficient use of a helper adenovirus of animal, preferably canine, origin.

In addition to the considerations for the quality of the viral stock produced, in a completely advantageous manner, the process according to the invention makes it possible to obtain particularly high virus titers. This is another completely remarkable property of the process according to the invention. Thus, the titers produced, which can exceed $10^{11}$ viral genomes per ml, are up to 1000 times greater than the titers observed in the prior art. These results are completely unexpected and are of vital importance in terms of industrial exploitation. The results are particularly remarkable with the cell lines derived from the line 293 and which express ORF6, optionally combined with ORF6/7, or the entire E4, under the control of the MMTV promoter (they therefore contain E1 expressed constitutively and E4 or part of E4 comprising at least ORF6 expressed conditionally in the presence of dexamethasone).

Even in the absence of any helper virus, these cell lines are capable of replicating AAV viruses. Thus, when these lines are infected with a wild-type AAV or when these lines are transfected with an infectious plasmid pAV2 (MacLaughlin, Gene, 23, 67–73, 1983), the AAV DNA can be caused to replicate. The efficiency of the replication of course remains lower than that obtained in the presence of a helper adenovirus, but demonstrates the particularly remarkable properties of the cells according to the invention.

A particularly advantageous cell line for carrying out the process according to the invention is represented by a cell line 293 comprising, inserted into its genome, a BglII-BglII fragment corresponding to nucleotides 34115–34290 of the genome of Ad5. This is for example a cell line 293 transformed by the plasmid pORF6Gen (Cf. examples).

By coinfecting a cell of this type with a helper adenovirus (for example a human helper adenovirus with a wild-type phenotype, or deleted for E1, or a double deletant for E1 and E4, or canine adenovirus), and by cotransfecting two plasmids: one AAV-plasmid, carrying the AAV ITRs flanking a nucleic acid of interest, and a plasmid carrying the rep and cap functions, infectious AAV virus particles can be produced at high titers in the presence of dexamethasone. As indicated in the examples, genome titers of $10^{11}$ genomes/ml can be obtained when the procedure is carried out on small quantities of cells. By carrying out the procedure on larger quantities of cells, higher titers can be obtained, up to $10^{12}$. Furthermore, by using the canine adenovirus as helper virus, the process of the invention makes it possible to have AAV stocks at high titers without contamination with human Ad.

Thus, another subject of the invention consists in a process for the production of recombinant AAVs characterized in that there is introduced into a culture of cells comprising, inserted into their genome, part of the E4 region of the genome of an adenovirus containing at least the reading frame ORF6:

an AAV plasmid carrying a nucleic acid of interest bordered by AAV ITRs, a helper adenovirus, and, the AAV rep and cap functions, and then the viruses produced are harvested.

According to a specific embodiment, the producing cell is a cell comprising the entire E4 region. According to another particularly advantageous embodiment, the producing cell is a cell containing part of the E4 region containing at least the reading frame ORF6 and optionally the reading frame ORF6/7. In a particularly preferred manner, this is a cell, as defined above, for the production of adenoviruses. In particular, it is advantageously a cell capable of transcomplementing the E1 and E4 functions of the adenovirus. A preferred example is represented by a cell line 293 containing, inserted into its genome, all the E4 region or part of the E4 region containing at least the reading frame ORF6 and optionally the reading frame ORF6/7. By way of example, there may be mentioned the clone#2 (IGRP2) and clone#4 (IGRP4) cells.

As indicated above, the helper adenovirus may be a human adenovirus with a wild-type phenotype, or which is defective for the E1 region, or a double deletant for E1 and E4, or alternatively canine adenovirus. The advantage of the process according to the invention lies, on the one hand, in the very high rAAV titers, and also in the safe character of the stocks which it makes it possible to produce. Thus, it is particularly advantageous to use a defective helper adenovirus, that is to say which is incapable of autonomously generating infectious particles. The helper adenovirus according to the process of the invention is advantageously a human adenovirus possessing a deletion in the E4 region. Still more preferably, it is a human adenovirus which is defective for the E1 and E4 regions. According to another advantageous embodiment, it is a canine adenovirus, preferably chosen from the CAV2 strains.

In the process according to the invention, the AAV rep and cap functions are preferably provided by cotransfection of the cells with a plasmid carrying the AAV rep and cap regions. These regions may be under the control of the homologous P5 promoter or of a constitutive promoter such as RSV-LTR. These functions may also be provided directly by the helper virus used. It is indeed possible to insert into the helper adenovirus a cassette containing the AAV rep and cap regions.

In the process of the invention, the transfection of the plasmid(s) (AAV-plasmid and RepCap-plasmid where appropriate) can be carried out by any technique known to persons skilled in the art. However, the better the transfection level, the more the production levels can be enhanced. In this regard, the applicant has now developed a method which is particularly efficient for the transfection of plasmids into the producing cells. This method is based use he use of a polycationic lipid and an agent which compacts the nucleic acids. One of the advantages of this method lies, in addition, in the fact that it does not appear to alter the morphology or the physiological state of the cells. Various types of cationic lipids can be used, such as lipofectamine, transfectam and the like. Among the DNA compacting agents, there may be advantageously mentioned peptides derived from nuclear proteins such as histones, nucleolin and the like.

The various plasmids and helper viruses can be introduced into the producing cell concomitantly or separately. In the case of a separate introduction, the order in which the various components are introduced does not appear to be essential for obtaining high titers. As illustrated in the examples, high titers were obtained when, in the first instance, the plasmids are cotransfected into the cells and then, in the second instance, the cells are infected by the helper virus.

A specific embodiment of the invention consists in a process for the production of recombinant AAVs, characterized in that, in a culture of the cells transcomplementing the adenovirus E1 and E4 functions, an AAV plasmid carrying a nucleic acid of interest bordered by AAV ITRs and a plasmid carrying the AAV rep and cap regions are cotransfected in the presence of a polycationic lipid and a compacting agent; the said culture is coinfected with a helper adenovirus chosen from human adenoviruses of Ad2 or Ad5 origin which are defective for the E1 and E4 regions and canine adenoviruses of CAV2 origin, and then the viruses produced are harvested.

This embodiment makes it possible to obtain high virus titers and stocks of pharmaceutical quality.

The present invention also relates to the purified viral preparations (adenovirus and AAV) obtained according to the process of the invention, as well as any pharmaceutical composition comprising one or more defective recombinant adenoviruses or AAVs prepared according to this process. The pharmaceutical compositions of the invention can be formulated for a topical, oral, parenteral, intranasal, intravenous, intramuscular, subcutaneous, intraocular or transdermal administration and the like.

Preferably, the pharmaceutical composition contains vehicles which are pharmaceutically acceptable for an injectable formulation. These may be in particular saline (monosodium or disodium phosphate, sodium, potassium, calcium or magnesium chloride and the like, or mixtures of such salts), sterile or isotonic solutions, or dry, especially freeze-dried, compositions which, upon addition depending on the case of sterilized water or physiological saline, allow the constitution of injectable solutions. Other excipients can be used, such as, for example a hydrogel. This hydrogel can be prepared from any bio-compatible and noncytotoxic polymer (homo or hetero). Such polymers have for example been described in Application WO93/08845. Some of them, such as especially those obtained from ethylene and/or propylene oxide, are commercially available. The virus doses used for the injection can be adjusted according to various parameters, and especially according to the mode of administration used, the relevant pathology, the gene to be expressed, or the desired duration of treatment. In general, the recombinant adenoviruses according to the invention are formulated and administered in the form of doses of between $10^4$ and $10^{14}$ pfu, and preferably $10^6$ to $10^{10}$ pfu and the AAVs between $10^6$ and $10^{11}$. The term pfu (plaque forming unit) corresponds to the infectivity of an adenovirus solution, and is determined by infecting an appropriate cell culture and measuring, generally after 15 days, the number of infected cell plaques. The techniques for determining the pfu titer of a viral solution are well documented in the literature.

Depending on the therapeutic gene, the viruses thus produced can be used for the treatment or the prevention of numerous pathologies, including genetic diseases (dystrophy, cystic fibrosis and the like), neurodegenerative diseases (Alzheimer, Parkinson, ALS and the like), cancers, pathologies linked to coagulation disorders or to dyslipoproteinemias, pathologies linked to viral infections (hepatitis, AIDS and the like), and the like.

The present invention will be more fully described with the aid of the following examples which should be considered as illustrative and nonlimiting.

LEGEND TO THE FIGURES

FIG. 1: Genetic organization of the Ad5 adenovirus. The complete sequence of Ad5 is available on a database and allows persons skilled in the art to select or create any restriction site, as well as to isolate any region of the genome.

FIG. 2: Genetic organization of the E4 region.

FIG. 3: Genetic organization of the E4 region in the defective E4 and wild-type adenoviruses. The size of the deletion is represented by a thick bar.

Figure 4A:
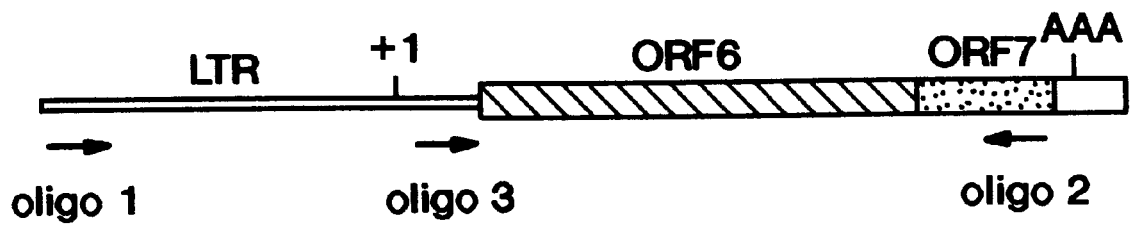
Figure 4B:
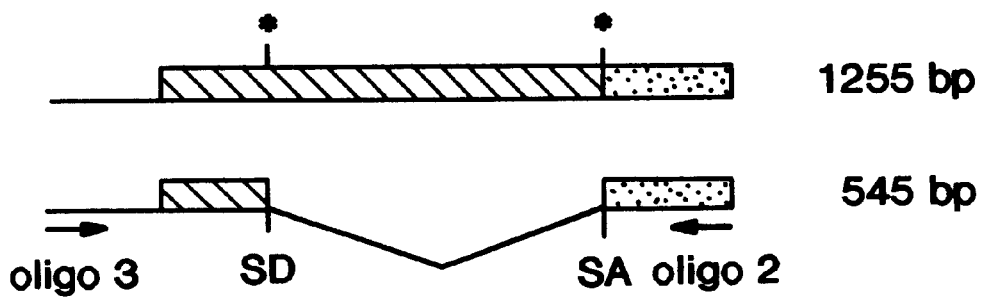

FIG. 4: (A) Schematic representation of the MMTV LTR/(ORF6+ORF7) cassette. The 1, 2 and 3 oligos used for the amplification or the RT-PCR are indicated. +1=site of initiation of transcription. AAA=polyadenylation site. (B) Structure of the products obtained by RT-PCR. SD=5' donor splicing site. SA=3' acceptor splicing site.

Figure 5:
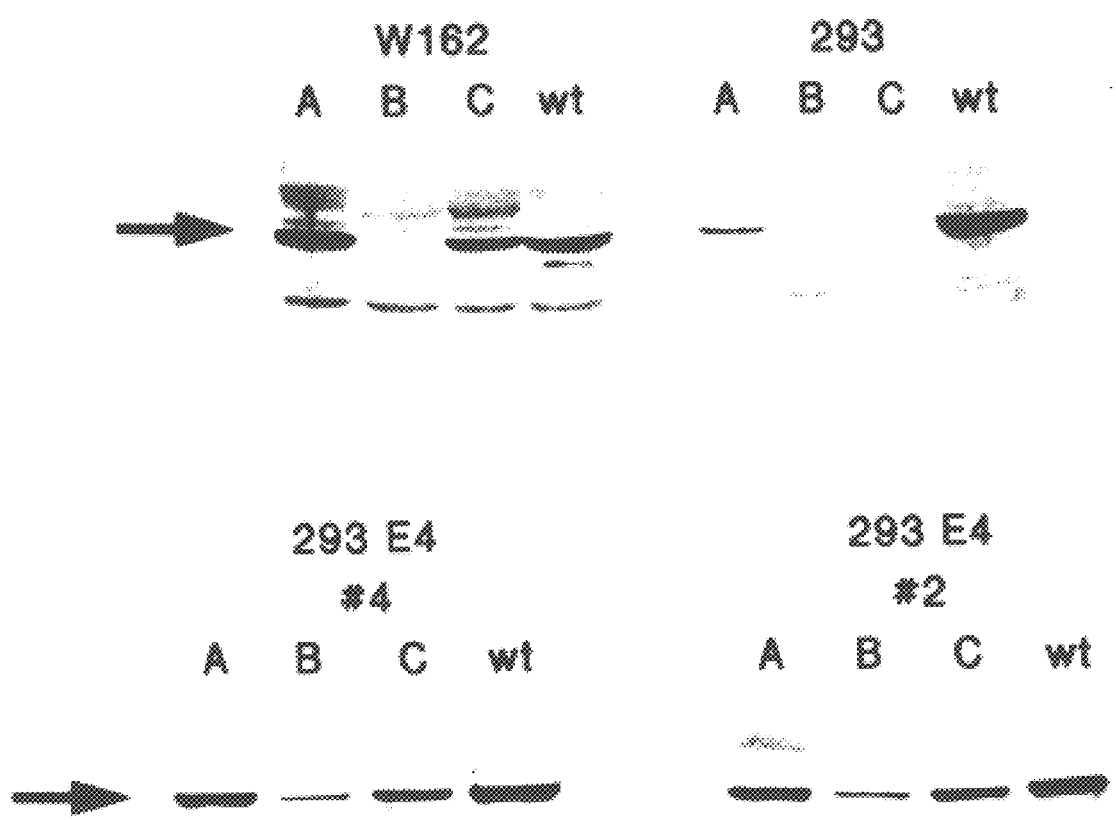

FIG. 5: Analysis of the production of the adenoviral fiber by immunological detection with the aid of a polyclonal serum against the fiber (Boulanger et al.). The cell extracts are prepared after 72 h of viral infection, the dexamethazone is added at the same time as the virus (final concentration 600 nM). (A) Infection by the virus dl1014 (MOI=10); (B) Infection by the virus dl1001 (MOI=1); Infection by the virus dl1004 (MOI=10); (wt) Infection by the virus Ad5 (MOI=10).

Figure 6:
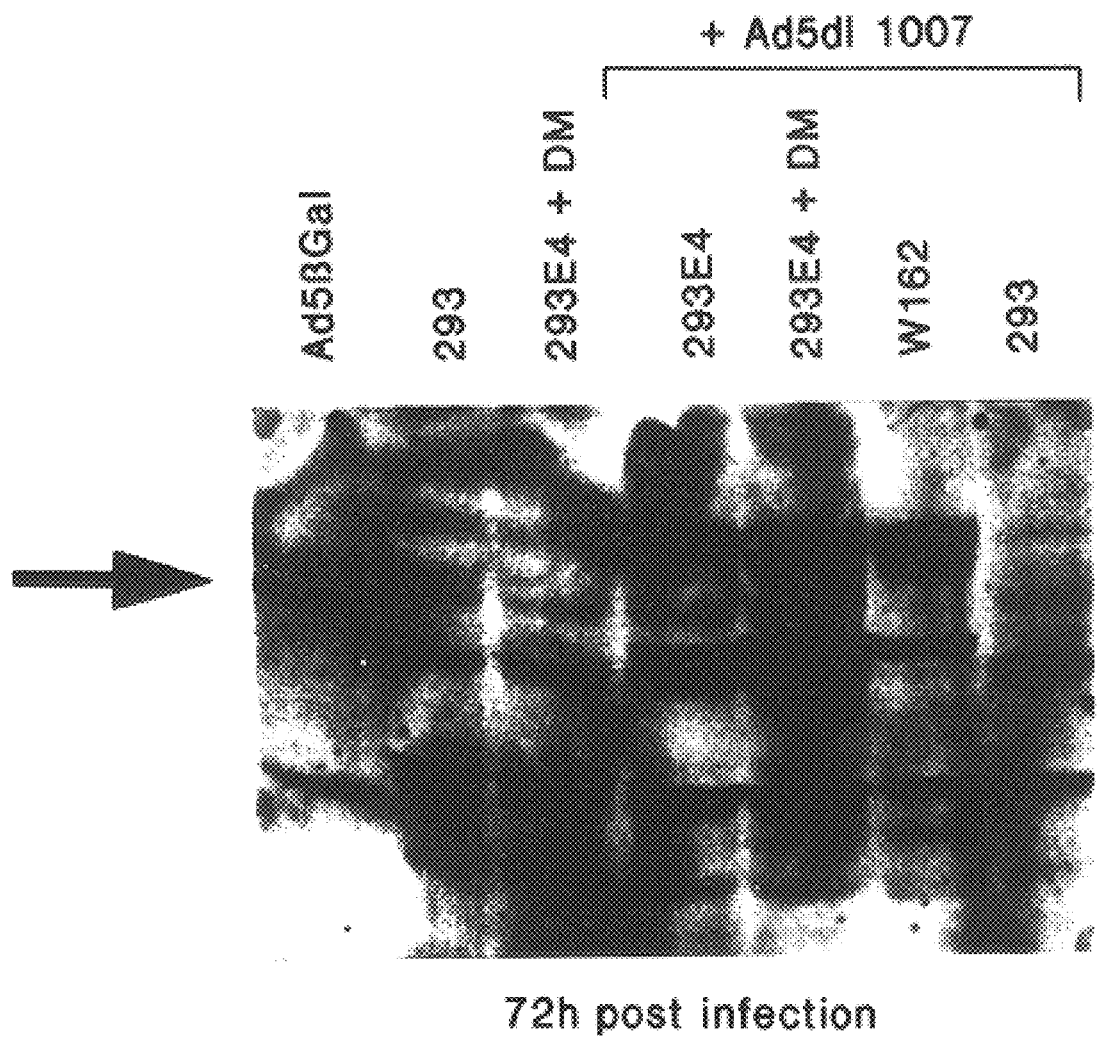

FIG. 6: Inducibility of E4 in the clone #2 cells. Analysis of the cell extracts uninfected (control less than 0) or infected by the virus dl1007, 72 h after infection. DM=dexamethazone (600 nM).

Figure 7:
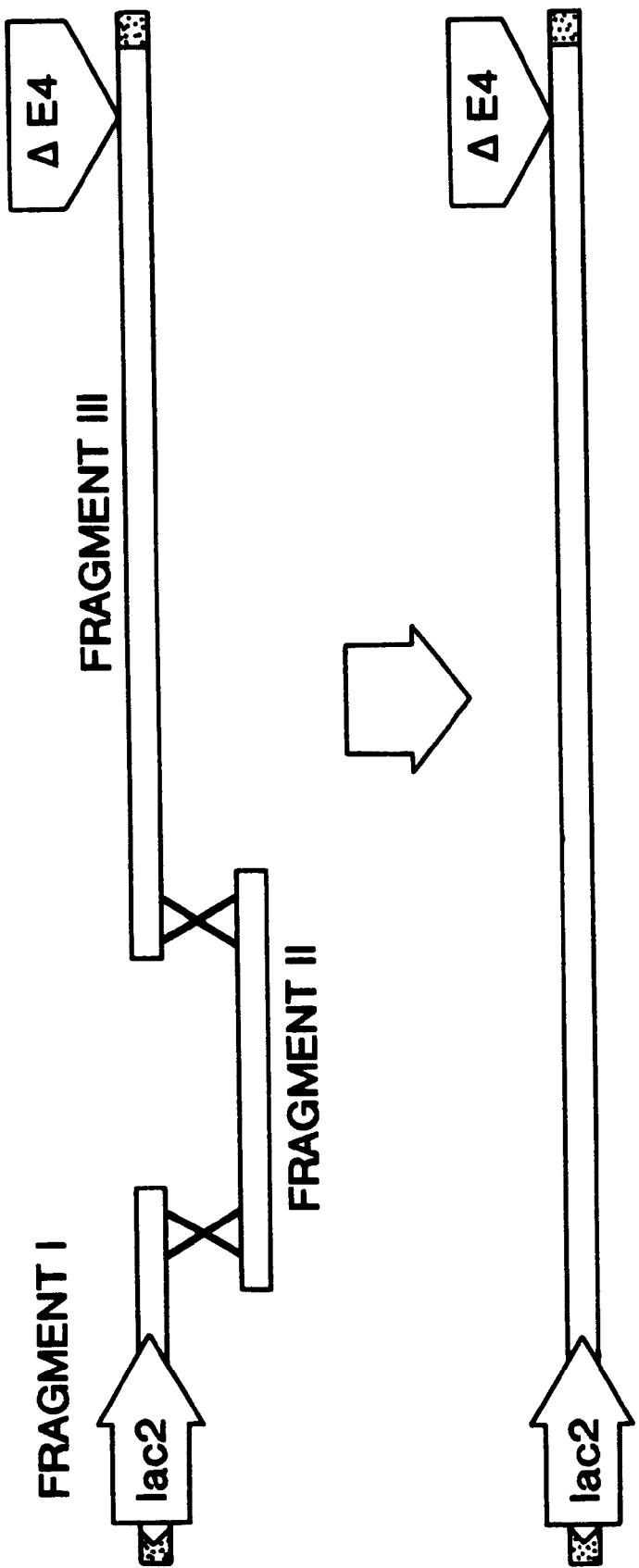

FIG. 7: Strategy for the clonal construction of the ΔE1, ΔE4 viruses.

GENERAL MOLECULAR BIOLOGY TECHNIQUES

The methods conventionally used in molecular biology, such as preparative extractions of plasmid DNA, centrifugation of plasmid DNA in cesium chloride gradient, agarose or acrylamide gel electrophoresis, purification of DNA fragments by electroelution, phenol or phenol-chloroform extraction of proteins, ethanol or isopropanol precipitation of DNA in saline medium, transformation in *Escherichia coli* and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al., (eds), "Current Protocols in Molecular Biology", John Wiley & Sons, New York, 1987].

The pBR322 and pUC type plasmids and the phages of the M13 series are of commercial origin (Bethesda Research Laboratories). For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier. The filling of the protruding 5' ends can be performed with the Klenow fragment of *E. coli* DNA polymerase I (Biolabs) according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method described by Taylor et al., [Nucleic Acids Res. 13 (1985) 8749–8764] using the kit distributed by Amersham. The enzymatic amplification of the DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] can be performed using a DNA thermal cycler (Perkin Elmer Cetus) according to the specifications of the manufacturer. The verification of the nucleotide sequences can be performed by the method developed by Sanger et al., [Proc. Natl. Acad. Sci. U.S.A., 74 (1977) 5463–5467] using the kit distributed by Amersham.

EXAMPLE 1

Construction of plasmids carrying various functional units of the E4 region under the control of a promoter 1.1. Construction of the plasmid pE4Gen The plasmid pPY2 corresponds to the cloning of the AvrII-SalI fragment (about 1.3 kb including the MMTV promoter) of the plasmid pMSG (Pharmacia) between the XbaI and SalI sites of the plasmid pIC20H prepared from a dam+ *E. coli* context. The plasmid pPY4 is derived from the plasmid pPY2 by deletion of a 35 bp fragment after coating with BamHI and BglII followed by religation. The plasmid pPY5 corresponds to the plasmid pIC20H in which the TaqI-BglII fragment including the E4 region of the type 5 adenovirus, situated between positions 35576 (TaqI) and 32490 (BglII), has been cloned between the ClaI and BamHI sites. The E4 region of the plasmid pPY5 is therefore included in an EcoRV and SphI fragment which can be cloned after partial digestion between the SmaI and SphI sites of the plasmid pPY4, generating the plasmid pPY6. The insertion of the XhoI fragment of the plasmid pKIXX (Pharmacia), which carries a gene conferring resistance to geneticin in the cells 293, into the plasmid pPY6 generates the plasmid pE4Gen. This plasmid therefore carries a selectable gene and the whole of the adenovirus E4 region expressed from the MMTV promoter. In this particular plasmid, these two genes follow each other and the respective coding sequences are carried by the same DNA strand. In this plasmid, the principal 5' donor splicing site located upstream of the reading frame ORF1 (towards position 35548) is therefore conserved in order to provide correct alternative splicing, making it possible to generate the various products of expression of all the coding frames of the E4 region and in a manner comparable to the alternative splicing observed during the viral cycle.

1.2. Construction of the plasmid pORF6Gen

The plasmid pPY13 corresponds to the cloning of the BglII-XbaI fragment of the plasmid pPY6 between the corresponding sites of the plasmid pIC20H. This 1.6 kb fragment therefore includes the type 5 adenovirus sequence from position 34115 (BglII) to position 32490 (BglII, followed by the XbaI site obtained from the multiple cloning site of the plasmid pIC20H). The plasmid pPY13 therefore contains the whole of the open reading frames ORF6 and ORF7 of the adenovirus, now included in an XhoI-SphI fragment. The cloning of this fragment between the SalI and SphI sites of the plasmid pPY4 generates the plasmid pPY15. The insertion of the XhoI fragment of the plasmid pKIXX, which carries a gene conferring the resistance to geneticin in the cells 293, into the plasmid pPY15 generates the plasmid pORF6Gen. This plasmid therefore carries a selectable gene and the open reading frames ORF6 and ORF7 of the adenovirus E4 region expressed from the MMTV promoter. In this particular plasmid, these two genes follow each other and the respective coding sequences are carried by the same DNA strand. The first codon for initiation of translation is that of the open frame ORF6 (position 34077 in the genome of Ad5), and it is separated from the CAP site of the MMTV promoter by 235 nucleotides. Since the alternative splicing is sequential and involves first of all the recognition of the 5' donor site, the principal 5' donor site located upstream of the reading frame ORF1 (toward position 35548) was not therefore included in the construction of the plasmid pORF6Gen so as to subsequently allow efficient expression of the products of the reading frames ORF6 and ORF6/7 (FIG. 4A).

1.3. Construction of the plasmid pORF4Gen

The plasmid pPY14 corresponds to the cloning of the 1.9 kb BglII-XbaI fragment (obtained after partial digestion with the enzyme BglII) of the plasmid pPY6 between the corresponding sites of the plasmid pIC20H. This 1.9 kb fragment therefore includes the type 5 adenovirus sequence from position 34387 (BglII) to position 32490 (BglII, followed by the XbaI site obtained from the multiple cloning site of the plasmid pIC20H). The plasmid pPY14 is therefore isogenic to the plasmid pPY13 except that is includes, in addition, a BglII fragment corresponding to virtually the whole of the open reading frame ORF4. This plasmid therefore contains the whole of the open reading frames ORF4, ORF6 and ORF7 of the adenovirus, now included in an XhoI-SphI fragment. The cloning of this fragment between the SalI and SphI sites of the plasmid pPY4 generates the plasmid pPY16. The insertion of the XhoI fragment of teh plasmid pKIXX, which carries a gene conferring the resistance to geneticin in the cells 293, into the plasmid pPY16 generates the plasmid pORF4Gen. This plasmid therefore carries a selectable gene and the open reading frames ORF4, ORF6 and ORF7 of the adenovirus E4 region expressed from the MMTV promoter. In this particular plasmid, these two genes follow each other and the respective coding sequences are carried by the same DNA strand. As with the plasmid pORF6Gen, the principal 5' donor site located upstream of the reading frame ORF1 (toward position 35548) was not included in the construction of the plasmid pORF4Gen so as to subsequently allow efficient expression of the products of the reading frames ORF4, ORF6 and ORF6/7.

1.4. Construction of the plasmids pJY1 and pJY2

This example describes the construction of a plasmid containing a functional unit of E4 (Cf. Example 1.2.) under the control of a promoter derived from MMTV. More particularly, this promoter is a derivative of MMTV comprising 5 elements for responding to glucocorticoids, that is to say a derivative which is highly inducible by the glucocorticoids. This plasmid was constructed in the following manner.

The BglII fragment of Ad5 (position 34115 to 32490) includes the sequences (ORF6+ORF7) of the E4 region. This fragment was first cloned between the BglII and BamHI sites of the plasmid pIC20H (Marsh et al., Gene 32 (1984) 481), generating the plasmid pPY13 in which the BglII site situated upstream of ORF6 is conserved. The BglII-SalI fragment of the plasmid pPY13 therefore includes the whole of the sequences (ORF6+ORF7) of the Ad5 E4 region. This fragment was cloned between the BamHI and SalI sites of the plasmid pIC20H, generating the plasmid pPY45.

The XbaI fragment (about 1 kb) of the plasmid pGRE5-1 (Mader and White, PNAS 90 (1993) 5603) corresponds to a promoter derived from MMTV, which is highly inducible by the glucocorticoids. This fragment was isolated and cloned between the XbaI sites of the plasmid pIC20H isolated from a dam-context. The plasmid obtained was designated pPY21. In this plasmid the BglII site obtained from the multiple cloning site of the plasmid pIC20H is located immediately upstream of the 5 promoter elements capable of binding the nuclear receptor to the glucocorticoids. The BglII-EcoRI fragment of the plasmid pPY21, containing the promoter which is highly inducible by glucocorticoids, was then cloned between the BglII and EcoRI sites of the plasmid pIC20H, generating the plasmid pPY26.

The cloning of the EcoRI-SphI fragment of the plasmid pPY45 between the corresponding sites of the plasmid pPY26 generates the plasmid pJY1 which contains the Ad5 sequences (ORF6+ORF7) under the control of the promoter which is highly inducible by glucocorticoids (pGRE5/(ORF6+ORF7) cassette).

A derivative of pJY1 was also constructed containing a geneticin resistance gene. The XhoI-SalI fragment of the plasmid pMSCV contains a bacterial gene conferring the resistance on eukaryotic cells to geneticin (APH), and which is expressed from a strong and ubiquitous promoter (PGK) in the cells. This fragment was cloned into the plasmid pJY1, at the SalI site. The plasmid obtained was designated pJY2. This plasmid contains the expression cassettes pGRE5/(ORF6+ORF7) and PGK/APH transcribed in the same direction.

1.5. Construction of the plasmid pGGO

The assembling of the GCR (HBD) and ORF6+ORF7 parts of the E4 region of Ad5 is performed after PCR amplification using the plasmid pSG5HGR as template and the deoxyoligonucleotides SEQ ID No. 5.

5'-GGCCCGCCGCCACCATGGAT
ATTGAACCTGAAGTGTTATATGCAGGA-3'.

(the SmaI site is in italics, the Kozak consensus sequence for initiation of translation is in bold type; the codon specifying residue 539 of GCR is underlined) and SEQ ID No. 6

5'-CTCGAGAACGCCGGACGTAGT
CTTTTGATGAAACAGAAG-3'

(the XhoI site is in italics, the TthIIII is in bold type; the codon specifying residue 777 of GCR is underlined). The oligonucleotide SEQ ID No. 5 therefore makes it possible to position an ATG specifying the initiation of translation upstream of the HBD domain of GCR, ranging from amino acids 539 to 777 of GCR. The oligonucleotide SEQ ID No. 6 makes it possible to position a restriction site TthIIII downstream of HBD. The PCR amplification fragment was first cloned into the commercial plasmid pCRII and the white-blue screening made it possible to select a clone whose identity was verified by sequencing (plasmid pCRII/GCR). This plasmid is therefore the source of an SmaI-XhoI fragment which carries the HBD domain of GCR having undergone PCR amplification with the oligos SEQ ID No. 5 and SEQ ID No. 6.

The plasmid pMEL3 is an intermediate construct which contains the EcoRI-PstI "polylinker" of the plasmid pSLII80 inserted between the EcoRI and PstI sites of a derivative of the plasmid pIC20H in which the HindIII site situated in the immediate vicinity of the NruI site on the "polylinker" has been treated with the Klenow fragment of Polymerase I of *E. coli* and then self-ligated, transforming the HindIII site to an NheI site. The plasmid pMEL3 also contains a BamHI fragment corresponding to the SV40 polyadenylation signal, previously inserted into the BglII site of the "polylinker" of pIC20H. The SmaI-XhoI fragment of the plasmid pCRII/GCR, which contains the HBD domain of GCR, was then inserted between the corresponding sites of the plasmid pMEL3, generating the plasmid pMEL3/GCR.

After total digestion of the plasmid pPY13 with HincII, partial digestion with SspI and then self-ligation of the plasmid, the plasmid pPY13 (ΔHincII-SspI) is generated which contains an HindIII fragment of about 1.4 kb containing the entire ORF6+ORF7 sequence of the E4 region of Ad5, including its polyadenylation site.

The plasmid pPY13 (ΔHincII-SspI) was digested with HindIII and its ends were filled using Klenow polymerase. This plasmid was then digested with XhoI, and the ORF6+ORF7 sequences (about 1.4 kb) are then cloned between the XhoI and NruI sites of the plasmid pMEL3/GCR, generating the plasmid pMEL3/GCR-TthIIII-(ORF6+ORF7).

The coupling of the TthIIII site introduced with the aid of the oligonucleotide SEQ ID No. 6 with the TthIIII site situated immediately downstream of the translational ATG of ORF6 on the Ad5 sequence (position 34070) makes it possible to carry out a translational coupling between the HBD domain of GCR and the ORF6 protein. The plasmid pMEL3/GCR-TthIIII-(ORF6+ORF7) is therefore digested with TthIIII and then self-ligated, generating the plasmid pMEL3/GCR- (ORF6+ORF7). This construct was sequenced in order to ensure translational coupling between the HBD domain of GCR and ORF6. The chimeric gene sequence obtained is presented sequence SEQ ID No. 7. That of the resulting protein GCR-ORF6 is represented sequence SEQ ID No. 8.

The treatment of the plasmid pPY26 with EcoRI and the Klenow fragment of polymerase I of *E. coli* and then with BglII generates a fragment including the inducible promoter GRE5, of which the cloning between the sites ApaI treated with the Klenow fragment and BamHI of the plasmid pMEL3/GCR-(ORF6+ORF7) generates the plasmid pMEL3/GRE-(GCR-ORF6+ORF7). This plasmid is the source of a BglII-NheI fragment corresponding to the expression cassette encoding the GCR-(ORF6+ORF7) fusion expressed from the GRE5 promoter and of which the cloning between the BglII and XbaI sites of the plasmid pCI-Neo (Promega) generates the plasmid pGG0.

EXAMPLE 2

Construction of the cell lines

This example describes the construction of complementing cell lines for the E1 and E4 regions of the adenoviruses according to the invention. These lines allow the construction and the propagation of recombinant adenoviruses deleted for these regions, without recourse to a helper virus.

The lines of the invention were constructed by cotransfection of the chosen cells in the presence of calcium phosphate, with the plasmids described in Example 1 and a construct encoding the glucocorticoid receptor (Hollenberg et al., Nature, 318, (1985) 635–641). More precisely, the cells of the line 293 in dishes 5 cm in diameter were transfected with 1 to 5 µg of E4 plasmid (pE4Gen, pORF6Gen, pORF4Gen, pGG0 or pJY2) and optionally 5 µg of a plasmid for the expression of the human glucocorticoid receptor expressed from the SV40 virus early promoter (plasmid pSG5HGR), in the presence of calcium phosphate, according to the procedure described by Graham and Van der Eb (Virology 52 (1973) 456).

2.1. Selection of the clones resistant to geneticin

After transfection of the cells, they are washed and then the culture medium (MEM, Sigma) supplemented with fetal calf serum (7% final) is added and the cells are left to incubate for 20 hours. The next day, the cells are selected in the presence of geneticin at the effective concentration of 350 mg/l. The geneticin is changed every three days and the selectable clones appear after about 3 weeks. When all the nontransfected cells are dead, only the cells into which the exist and to ne has been inserted continue to exist and to divide in order to generate the cell clones. When the cell clones are sufficiently big so that they are visible to the naked eye, they are individually transferred into the culture wells of a "24-slot" culture plate. Each clone is then gradually amplified in the presence of geneticin, first in the wells of a "12-slot" culture plate and then in the wells of a "6-slot" culture plate and then amplified in cell culture dishes. Each cell clone is then preserved by freezing in liquid nitrogen.

2.2. Selection of the clones capable of producing viruses deficient for E4

The adenoviruses Ad2dl808 (Weinberg and Ketner, J. Virol. 57 (1986) 833), Ad5dl1004, dl1007 or dl1014 (Bridge and Ketner, J. Virol. 63 (1989) 631), dl1011 (Bridge et al., Virology 193 (1993) 794) are deletion mutants carrying major deletions at the level of the E4 region. These mutants are incapable of replicating in the cells 293, but can be produced in the W162 cells (Weinberg and Ketner, PNAS 80 (1983) 5383). In a second stage, the 50 clones resistant to geneticin were tested for their capacity to produce these E4⁻ viruses and therefore to transcomplement the E4 region. 60 clones transfected with the plasmid pJY2, which is resistant to geneticin, were also screened for this capacity to transcomplement the E4 region.

For that, each clone is infected in a liquid medium with the dl808 virus at a multiplicity of infection of about 0.1 pfu/cell (the viral titer is obtained on the W162 line). The infection was carried out at an moi of 0.5 pfu/cell for the pJY2 clones, in a medium supplemented with dexamethazone (1 µM). The appearance of a cytopathic effect amplifiable by successive reinfection of the cells with the cell lysate obtained is indicative of some viral propagation of dl808 by the cells of the clone considered. This transcomplementation is then objectivized both by analyzing the level of viral replication and the ability of the cells to form viral plaques (a possible procedure is described by Hitt, M.; Bett, A. J.; Prevec, L. and Graham, F. L. "Construction and propagation of human adenovirus vectors" in: Cell Biology; a Laboratory Handbook. Volume 1, J. E. Celis (Ed); Academic Press Inc. (San Diego, Calif., U.S.A.). p479–490) after infection with dl808.

This step made it possible to detect several specific clones having efficient properties in relation to the transcomplementation of the E4 region. The first, designated clone#2, results from the transfection of the plasmid pORF6Gen; the second, designated clone#4, was isolated after transfection of the plasmid pE4Gen. Stable clones, capable of transcomplementing for the E4 region, and highly inducible by glucocorticoids were also obtained after transfection of the cells 293 by the plasmid pJY2. Moreover, other stable clones, capable of efficiently propagating viruses defective for the E4 region, and highly inducible by a nonsteroidal compound were further prepared. These clones were obtained by cotransfecting the cells 293 with the plasmid pJY2 and with a plasmid expressing an artificial transactivator composed of a transactivating region (VP16), the region which binds the DNA obtained from the glucocorticoid receptor, and part of the progesterone receptor which is truncated at the C terminus, such that this hybrid receptor is capable of transactivating the GRE5 promoter in the presence of RU486 and not of steroids. The clones obtained are effectively capable of efficiently propagating defective E4-viruses in the presence of RU486.

The plasmid pGG0 alone or in equimolar combination of the plasmids pGG0 and pSG5HGR are transfected into cells permissive for the type 2 or 5 adenovirus, and the stable clones are selected in the presence of 400 mg/l of geneticin. For example, the transfection of the plasmid pGG0 into the cells 293 generates the clone IGRP18 which allows the propagation of the viruses doubly defective for E1 and E4 in the presence of dexamethasone (1 µM), which is not the case in the absence of addition.

2.3. Capacity to propagate adenoviruses deficient for E1

The capacity of the prepared lines to complement the E1 region was verified after infection with the adenovirus Ad-RSVβGal. This first generation adenovirus (deficient in E1 only) comprises the *E. coli* LacZ gene under the control of the RSV virus LTR promoter (Stratford-Perricaudet et al., J. Clin. Invest. 90 (1992) 626). The cells of clones#2, #4 and cells obtained with pJY2 were infected with the virus Ad-RSVβGal and a viral propagation was observed for each clone.

These results show that the capacity of the cells to transcomplement the E1 region was not affected by the additional introduction of the distal part of the E4 region (clone#2, pJY2 cells) or of the complete E4 region (clone #4).

2.4. Southern, Northern-blot and RT-PCR analysis to check the integration of a functional E4 unit into the genome The cells of clones #2 and #4 were analyzed by Southern-blotting to check the expression of the viral proteins. More particularly, the Southern-blot analysis (analysis of the genomic DNA hybridizing with a radioactive probe obtained from the adenoviral E4 region) was carried out according to the procedure described by Maniatis et al. In this regard, the genomic DNA of the cells 293 and #2 was prepared. 2 µg of this DNA were used as template in a PCR reaction carried out in the presence of Taq polymerase, oligo 1 of sequence SEQ ID No. 1 (corresponding to nucleotides 52 to 71 of the MMTV promoter) and oligo 2 of sequence SEQ ID No. 2 (corresponding to positions 32921–32940 of the Ad5 genome). These oligos amplify a 2617 bp fragment of the plasmid pORF6Gen. The amplification was carried out under the following conditions: denaturation at 94° C. for 5 min, 30 amplification cycles by denaturation at 94° C. for 1 min, annealing at 60° C. for 2 min, and extension at 70° C. for 3 min, the extension during the last cycle being prolonged for 10 min. The amplification products were then analyzed by SDS 1% agarose gel electrophoresis and identified by Southern blotting and hybridization with a labeled probe covering the (ORF6+ORF7) region of the adenovirus or the MMTV region.

The Northern-blot and RT-PCR analysis (analysis of the cellular RNAs of clones 2 and 4 which hybridize with a radioactive probe obtained from the adenovirus E4 region) were carried out according to the procedure described by Maniatis et al., the polyadenylated cellular RNAs having been prepared according to the procedure described by R. E. Farrell Jr. "RNA isolation strategies". in: RNA Methodologies; a Laboratory Guide for Isolation and Characterization. Academic Press Inc. (San Diego, Calif. U.S.A.). p.46–92). For the RT-PCR, 500 ng of the polyA$^+$ RNAs were treated with 0.5 unit of DNAse I and then subjected to reverse transcription with an oligo(dT) primer. A tenth of the single-stranded cDNA preparation thus obtained was used as template in a PCR reaction carried out using oligo 2 (SEQ ID No. 2) and oligo 3 (SEQ ID No. 3), corresponding to nucleotides 227–246 relative to the cap site of the MMTV promoter (see FIG. 4). These oligos were constructed in order to amplify a 1255 bp fragment of the nonspliced mRNA ORF6 and a 545 bp fragment of the spliced mRNA ORF6/7. The amplification products were analyzed on an SDS 1% agarose gel and identified by Southern blotting and hybridization to the labeled probe (ORF6+ORF7).

These analyses made it possible to show that these 2 clones possess their respective functional E4 unit integrated in an amount of a few copies per cell. Furthermore, these studies demonstrate that these two clones express the protein of the adenovirus fiber after infection with the deletion mutants Ad5dl1004, Ad5dl1011 and Ad5dl1014 (FIG. 5). This protein is a late protein of the replicative and infectious cycle of the adenovirus whose synthesis involves the expression of E4. The presence of this protein in the cells infected by the E4$^-$ mutants confirms that these cells indeed express a functional E4 activity.

The Southern-blot analyses indicate more particularly that clone#2 contains a copy of the MMTV-(ORF6+ORF7) cassette integrated into its genome. The integrity of this cassette was, in addition, demonstrated by the amplification using oligos 1 and 2 which generates an expected 2.6 kb fragment, which can be specifically detected by a radiolabeled probe corresponding to the (ORF6+ORF7) unit or to the MMTV promoter (FIG. 4). The occurrence of a correct alternative splicing in the cells of the invention was also demonstrated by RT-PCR. Thus, 2 principal signals were specifically detected with the radiolabeled probe (ORF6+ORF7) in the noninfected clone#2 cultivated in the presence of dexamethazone (inducing conditions). The largest signal is a fragment of about 1.3 kb, a size which corresponds perfectly to a nonspliced product derived from ORF6/ORF7. The other signal is a fragment of about 0.6 kb, a size which is in agreement with the excision (during the splicing) of the intron of 712 nucleotides generating the messenger ORF6/7. These results show clearly that a correct alternative splicing occurs in the cells of the invention, and that the two products ORF6 and ORF6/7 of the E4 region are indeed expressed in these cells.

The capacity of the cells of the invention to express a functional product of the ORF6 region was moreover demonstrated by immunodetection of the protein of the fiber. The results obtained show that the cells 293 infected by the adenovirus Ad5dl1007 do not produce fibers. In contrast, a fiber-specific signal is detected in the cells of the invention (especially clone#2) after infection with this mutant, and not in the other noninfected cells. The presence of the fiber was also demonstrated in the cells of the invention infected with the mutants dl808, dl1004 (ORF1$^+$), dl1011 or dl1014 (ORF4$^+$) in the presence of dexamethazone.

2.5 Formation of plaques

This analysis shows clearly the particularly advantageous properties of the lines according to the invention. Indeed, whereas the two clones (clone#2 and clone#4) are capable of transcomplementing the E4 region and of propagating with a comparable efficiency the mutants Ad2dl808 or Ad5dl1004 for example, they exhibit a very significant difference as regards the formation of virus plaques after infection with the mutants Ad2dl808, Ad5dl1004, Ad5dl1007, Ad5dl1011 or Ad5dl1014.

The capacity to form virus plaques is an essential property of the producing lines. It is indeed under this condition that recombinant virus clones can be isolated, then amplified and purified. The results obtained show clearly that the formation of virus plaques is always observed with clone#2, whereas this occurs only rarely with clone#4. These results demonstrate clearly the highly superior properties of the lines of the invention into which only a specific functional unit of the E4 region is integrated.

2.6. Regulated expression of the E4 activity

Another advantageous property of the clone#2 according to the invention lies in the regulated and inducible character of the expression of the E4 activity. Thus, the results obtained show that the formation of virus plaques is observed only in the presence of dexamethazone. Likewise, in clone#2, the expression of the adenovirus fiber protein after infection with the mutant Ad5dl1007 is significantly enhanced under induction conditions (FIG. 6). The same results were obtained with the mutants Ad5dl808, Ad5dl1004, Ad5dl1011 and Ad5dl1014. On the other hand, the expression of the E4 activity in clone#4 is constitutive.

These results as a whole demonstrate clearly the advantages of the cell lines of the invention into which only a specific functional unit of the E4 region is integrated. These advantages lie in particular in the capacity to form virus plaques and to allow the amplification of the defective viruses in liquid medium. These advantages also exist in the regulated character of the expression of the E4 activity, contrary to the lines in which larger functional units of E4 are present.

EXAMPLE 3

Production of viruses defective for the E1 and E4 functions

This example describes the use of the cell lines according to the invention for the production of recombinant viruses deficient in the E1 and E4 regions. These adenoviruses were produced by homologous recombination, after cotransfection, in the cells of the invention, of two DNA fragments, one providing the left part of the genome of the recombinant virus (possessing a deletion in the E1 region), the other providing the right part of the genome of the recombinant virus (possessing a deletion in the E4 region).

More precisely, the 293E4 cells (clone#2 and #4) were cotransfected with 10 mg of Ad-RSVβGal virus DNA (Stratford-Perricaudet et al.) digested with SrfI (or 5 mg of plasmid DNA having served for the construction of this virus and digested with XmnI), and 10 mg of the virus DNA providing the functional deletion of the E4 region (for example Ad2dl808, Ad5dl1004, Ad5dl1007 or Ad5dl1014) digested with the enzyme ClaI. After the appearance of the cytopathic effect, the viruses are purified by at least two consecutive cycles of plating on solid medium for the formation of plaques on clone 2. The plaques corresponding to the infection of the desired virus (analysis of the DNA demonstrating the double deletion E1 and E4) are then amplified by consecutive cycles of infection. Stocks at high titers are prepared by purification on a cesium chloride gradient. The viruses are preserved at −80° C. according to conventional techniques used by persons skilled in the art.

In addition to the ability of clone 2 to make viral plaques, it allows a perfectly efficient propagation in liquid medium for the virus Ad5dl1014 (E1$^+$E4$^-$ but ORF4$^+$) or for the virus E1$^-$E4$^-$ constructed from the virus dl1014.

On the other hand, the clone 4 obtained after transfection of the plasmid pE4Gen is not very efficient for making plaques because it has difficulty sustaining cellular confluence for a period which is sufficiently long for the viral lyses plaques to be easily identifiable (and especially if the desired recombinant virus does not encode β-galactosidase).

An alternative method of production is based on the clonal construction of the viruses according to the invention. More particularly, according to this method, the adenoviruses ΔE1ΔE4 are produced by double homologous recombination in vivo after cotransfection of 3 overlapping DNA fragments, each providing part of the virus genome.

More particularly, the following 3 overlapping fragments, derived from the AdRSVβgal and Ad dl1014 genomes, were purified by electroelution (FIG. 7):

i) Fragment I: This fragment is a 6.8 kb NarI fragment encoding βgal corresponding to the left part (ΔE1) of the genome of AdRSVβgal. Its contamination by an uncut (and therefore replicative) AdRSVβgal genome is highly improbable because complete digestion with NarI generates this fragment among 25 others ranging from 26 nucleotides to 3.8 kb.

ii) Fragment II: This fragment is a 9.4 kb DraI fragment which is also derived from the genome of AdRSVβgal, and which overlaps with fragment I over 1509 nucleotides (cf. FIG. 7). The contamination of this fragment by an infectious genome is also impossible since this fragment was purified from 10 additional fragments with a size of between 494 nucleotides and 4.8 kb, after total digestion with DraI and AflII.

iii) Fragment III: This fragment is a 21.3 kb NsiI fragment derived from the genome of Ad5dl1014. It overlaps with the fragment II over 1652 nucleotides (FIG. 7). This fragment provides the right part of the genome of the recombinant virus, containing the modified E4 region (ΔE4,ORF4$^+$). Its contamination is once again more than improbable since it was purified after complete digestion with NsiI generating 7 fragments with a size of between 178 nucleotides and 4 kb.

The purified fragments were cotransfected into the clone#2 cells according to the procedure described for the cells 293, in the presence of 1 μM of dexamethazone in the medium (added every 4 days for 3 weeks). At the end of this culture, the cells were harvested, frozen and thawed 3 times in an ice/ethanol bath and then centrifuged at 3000 g for 20 min. The cell lysate was then added to a fresh culture of clone#2 (also designated IGRP2) cells in the presence of dexamethazone (1 μM). After 5 days, a cytopathic effect was observed, demonstrating the production of the viruses. A stock of this recombinant virus AdΔE1, ΔE4, ORF4$^+$ was obtained after gradual amplification of the mixture inducing the cytopathic effect on 100 10-cm dishes containing clone#2 cells at subconfluence, in the presence of 1 μM dexamethazone. After purification on a cesium chloride gradient and dialysis at 4° C., the viral stock was titrated on monolayers of clone#2 cells supplemented with dexamethazone (1 μM), before staining in vitro with X-Gal. Since all the plaques are positive, the titer can be expressed either in pfu/ml or as viral plaque expressing β-gal. According to this procedure, a stock of 10$^{10}$ pfu was prepared. The absence of RCA in this stock was then checked by restriction and Southern-blot analyses. For that, the viral DNA of a recombinant from the stock was prepared according to the technique of Challberg (Virology 114 (1981) 196). 2 μg of this DNA were subjected to restriction analysis and 1% agarose gel. The fragments were transferred onto a Hybond-N membrane (Amersham) and hybridized with a radioactive probe corresponding to the adenovirus ITR(s) in order to detect specifically the fragments located at the ends of the viral genome.

The restriction analysis with the SmaI, AflII or StuI enzymes gave the expected profiles, for preparations not contaminated by E1$^+$ or E4$^+$ fragments as shown by the relative stoichiometry of the various restriction fragments.

The Southern analysis after transfer onto membranes shows that the digestion with StuI generates only 2 fragments which hybridize with the ITR probe: one of these fragments has a mobility corresponding to that of the 1125 bp fragment of AdRSVβgal encoding βgal, the other migrates like the 2673 bp StuI fragment of Ad5dl1014 carrying the E4 deletion. A prolonged exposure of the autoradiogram reveals no additional band having a size corresponding to the fragment E1$^+$ (3158 bp) or E4$^+$ (3980 bp). Likewise, a fragment corresponding in size (3267 bp) to the introduction of the functional E4 unit (ORF4+ORF6+ORF7) into the genome of the recombinant was not detected, demonstrating that there was no double recombination event during the production between the viral genome and the E4 unit integrated into the cell. These results therefore demonstrate that the cells of the invention can be used to produce efficiently batches of ΔE1, ΔE4 viruses free of RCA.

EXAMPLE 4

Production of recombinant AAVs

This example describes the use of the cell lines containing all or part of the E4 region of an adenoviral genome for the production of AAVs. These AAVs were produced by cotransfection, into the cells, of an AAV-ITR plasmid and a Rep/Cap plasmid, and by coinfection with a helper adenovirus.

Plasmids and viruses used

AAV-ITR plasmid, designates pMA10: this plasmid contains a nucleic acid of interest (cassette for the expression of the *E. coli* β-gal gene, composed of the RSV-LTR promoter, the LacZ gene preceded by a nuclear localization signal, and the SV40 virus polyadenylation site) bordered by 2 AAV ITRs. The plasmid pMA10 was obtained by digesting the plasmid pXL2582 with SpeI and ligating by treating with T4 bacteriophage DNA ligase. This treatment makes it possible to eliminate the palindromic sequences downstream of the left AAV ITR. The plasmid pXL2582 was obtained by ligating the following fragments in the EcoRI-KpnI sites of pXL2359 (described in Application FR94 02445):

a) EcoRI-XbaI (containing the left AAV ITR up to nucleotide 155, HinfI site in the published AAV sequence) of pXL2580, and, b) XbaI-KpnI of pXL2359 (containing the cassette for the expression of the LacZ gene).

The plasmid pXL2580 was obtained from pXL2359 in the following manner: pXL2359 was digested with EcoRI-XbaI and deposited on a 1% agarose gel, from which a 650 bp fragment was purified. This fragment was redigested with HinfI and treated with T4 bacteriophage DNA polymerase, recut with PstI and then deposited on a 2% agarose gel, from which a 200 bp fragment was purified. This fragment, containing the left AAV ITR up to nucleotide 155, was introduced between the PstI-SmaI sites of pBSKS+ (Stratagene).

Rep/Cap plasmid: the plasmid used, designated pΔBal, has been described by Lebkowski et al., (Mol. Cel. Biol. 8 (1988) 3988). This plasmid contains the AAV rep and cap regions under the control of the endogenous promoter P5. Other promoters can be substituted for the P5 promoter, such as especially the constitutive RSV-LTR promoter.

The helper adenovirus used is a wild-type Ad5 adenovirus. It is understood that other helper viruses can be used, and especially an Ad5 defective for the E1 and/or E4 region, or a canine adenovirus. The benefit of using a canine adenovirus lies in their capacity to support the replication of AAVs while being defective viruses in man. As a result, the rAAV preparations obtained are totally free of RCA and of contaminating human adenovirus.

Procedure

The production was carried out by transfecting 20 dishes, 5 cm in diameter, of clone#2 cells (IGRP2), at the density of about $3 \times 10^6$ cells per dish, previously inoculated 24 to 48 hours in MEM 10% FCS medium. In each dish, 1 µg of plasmid pMA10 and 5 µg of plasmid pΔBal were cotransfected in the presence of 16 µg of peptide H1, 16.5 µl of lipofectamine (Gibco-BRL, Life Technologies) and of OPTIMEM lipofectamine (Gibco-BRL, Life Technologies) according to the recommendations of the supplier. After 4 to 16 hours of contact between the mixture and the cells, the transfection mixture was withdrawn and the cells were infected for one hour with the helper adenovirus, with an infectivity of 10 pfu of virus per cell in a final volume of 500 µl. MEM 10% FCS+$10^6$ M dexamethasone medium was then added. The cells were harvested 5 days later, taken up in 10 mM Tris-HCl buffer, pH 8, lysed by 3 freeze-thaw cycles and then treated with sodium deoxycholate and with trypsin at the respective concentrations of 0.25% and 1% for 30 min at 37° C. The recombinant AAVs produced were then purified on a cesium chloride gradient at the density of 1.4, in an SW55.1 rotor at 35,000 rpm for 20 hours.

These experiments made it possible to obtain high recombinant virus titers: $10^{11}$ genomes per ml. This process therefore makes it possible to produce very large quantities of recombinant AAVs (the processes described in the prior art lead to titers which are 10 to 100 times lower), having qualities appropriate for therapeutic use in man. In addition, it is very easy to use quantities of cells which are 10 times greater, and therefore to obtain a higher virus titer.

We claim:

1. A recombinant cell line for the production of a defective adenovirus comprising, inserted into its genome, part of an adenovirus E4 region comprising an ORF6 reading frame under the control of a functional promoter, wherein the inserted E4 region does not contain a functional ORF4 reading frame.

2. The cell line according to claim 1, wherein the E4 region further comprises a reading frame ORF6/7.

3. The cell line according to claim 1, wherein the E4 region is derived from a group C human adenovirus genome.

4. The cell line according to claim 3, wherein the E4 region is derived from the genome of an Ad2 or Ad5 adenovirus.

5. The cell line according to claim 1, wherein the promoter is an inducible promoter.

6. The cell line according to claim 5, wherein the promoter is an MMTV promoter.

7. The cell line according to claim 1, wherein the reading frame ORF6 is fused in translational phase with a domain of a nuclear receptor responsible for recognizing its specific ligand.

8. The cell line according to claim 7, wherein the nuclear receptor domain is a hormone-binding domain of the glucocorticoid receptor (HBD-GCR).

9. The cell line according to claim 8, wherein the reading frame ORF6 fused in translational phase with the domain of a nuclear receptor responsible for recognizing its specific ligand is placed under the control of an inducible promoter which responds to a glucocorticoid.

10. The cell line according to claim 9, wherein the inducible promoter is a GRE5 promoter.

11. The cell line according to claim 1, which transcomplements for the E1 region.

12. The cell line according to claim 11, which is derived from cell line 293.

13. The cell line according to claim 1, which is derived from a cell line selected from the group consisting of KB, Hela, MDCK, Vero, or gmDBP6 cells.

14. The cell line according to claim 1, which is derived from a culture of primary cells.

15. The cell line according to claim 1, wherein the part of the E4 region does not contain ORF4.

16. The cell line according to claim 15, wherein the part of the E4 region does not contain ORF1-ORF4.

17. The cell line according to claim 1, wherein the part of the E4 region is a BglII-BglII fragment corresponding to nucleotides 34115–32490 of the Ad5 genome, or the corresponding nucleotides from Ad2, Ad7 or Ad 12.

18. The cell line according to claim 17, which is a cell of a 293 line.

19. The cell line according to claim 1, wherein the part of the E4 region is a BglII-PvuII fragment corresponding to nucleotides 34115–33126 of the Ad5 genome, or the corresponding nucleotides from Ad2, Ad7 or Ad12.

20. A plasmid comprising part of an E4 region of an adenovirus genome carrying a reading frame ORF6 under the control of an inducible promoter.

21. The plasmid according to claim 20, wherein the E4 region further comprises a reading frame ORF6/7.

22. The plasmid according to claim 20, wherein the reading frame ORF6 is fused in translational phase with a domain of a nuclear receptor responsible for recognizing its specific ligand.

23. A method for the production of a recombinant adenovirus which is defective at least for the E4 region, comprising infecting the cell line of claim 1 with the E4 defective adenovirus and harvesting the virus.

24. The method according to claim 23, wherein the cell line cells are transformed with one or more plasmids providing the various regions of the genome of the defective recombinant adenovirus.

25. The method according to claim 24, wherein the recombinant adenovirus is defective for E1 and E4 regions.

26. A defective recombinant adenovirus ΔE1,ORF3+, ORF6−, wherein all or part of the E1 region and of nucleotides 34801–34329 and 34115–33126 of the Ad5 E4 region, or the corresponding nucleotides from Ad2, Ad7 or Ad12, are deleted.

27. A defective recombinant adenovirus ΔE1,ΔE4,ORF1+, wherein all or part of the E1 region and the E4 region with the exception of reading frame ORF1 are deleted.

28. The defective recombinant adenovirus according to claim 27, wherein a fragment whose 5' end is contained in the reading frame ORF7 and whose 3' end is situated in the reading frame ORF2 is deleted.

29. The defective recombinant adenovirus according to claim 28, wherein the Ad5 E4 region covering nucleotides 33093 to 35053, or the corresponding region from Ad2, Ad7 or Ad12, is deleted.

30. A defective recombinant adenovirus ΔE1,ΔE4,ORF4+, wherein all or part of the E1 region and the E4 region with the exception of the reading frame ORF4 are deleted.

31. The defective recombinant adenovirus according to claim 30, wherein the E1 region, a fragment whose 5' end is contained in the reading frame ORF7 and whose 3' end is situated in the reading frame ORF6, and a fragment whose 5' end is contained in the reading frame ORF3 and whose 3' end is situated in the reading frame ORF1 or in the E4 promoter region are deleted.

32. The defective recombinant adenovirus according to claim 31, wherein nucleotides 33093(SmaI)–33695 and nucleotides 34634–35355(SmaI) of the Ad5 E4 region, or the corresponding nucleotides from Ad2, Ad7 or Ad12, are deleted.

33. A defective recombinant adenovirus ΔE1,ΔE4, wherein all or part of the E1 region and the whole of the E4 region, chosen from the group consisting of Ad5 nucleotides 33466–35355 and 33093–35355, or the corresponding nucleotides from Ad2, Ad7 or Ad12, are deleted.

* * * * *